United States Patent
Brekke et al.

(10) Patent No.: US 9,901,635 B2
(45) Date of Patent: Feb. 27, 2018

(54) VACCINES AGAINST HPV

(71) Applicant: Vaccibody AS, Oslo (NO)

(72) Inventors: Ole Henrik Brekke, Oslo (NO);
Agnete Brunsvik Fredriksen, Raelingen (NO); Ali Areffard, Oslo (NO); Mona Mari Lindeberg, Oslo (NO)

(73) Assignee: Vaccibody AS, Oslo (NO)

( * ) Notice: Subject to any disclaimer, the term of this patent is extended or adjusted under 35 U.S.C. 154(b) by 0 days.

(21) Appl. No.: 14/365,536

(22) PCT Filed: Dec. 20, 2012

(86) PCT No.: PCT/EP2012/076404
§ 371 (c)(1),
(2) Date: Jun. 13, 2014

(87) PCT Pub. No.: WO2013/092875
PCT Pub. Date: Jun. 27, 2013

(65) Prior Publication Data
US 2015/0056197 A1    Feb. 26, 2015
US 2015/0306217 A9    Oct. 29, 2015

Related U.S. Application Data

(60) Provisional application No. 61/578,542, filed on Dec. 21, 2011.

(51) Int. Cl.
| | |
|---|---|
| *A61K 39/12* | (2006.01) |
| *C07K 14/025* | (2006.01) |
| *A61K 39/395* | (2006.01) |
| *A61K 39/00* | (2006.01) |
| *C07K 14/52* | (2006.01) |
| *C07K 14/005* | (2006.01) |
| *C07K 16/08* | (2006.01) |
| *C12N 7/00* | (2006.01) |
| *A61K 48/00* | (2006.01) |

(52) U.S. Cl.
CPC .... *A61K 39/39575* (2013.01); *A61K 39/0011* (2013.01); *A61K 39/12* (2013.01); *C07K 14/005* (2013.01); *C07K 14/523* (2013.01); *C07K 16/084* (2013.01); *C12N 7/00* (2013.01); *A61K 48/00* (2013.01); *A61K 2039/505* (2013.01); *A61K 2039/53* (2013.01); *A61K 2039/585* (2013.01); *A61K 2039/6031* (2013.01); *A61K 2039/6056* (2013.01); *A61K 2039/64* (2013.01); *C07K 2317/526* (2013.01); *C07K 2317/53* (2013.01); *C07K 2319/00* (2013.01); *C07K 2319/02* (2013.01); *C07K 2319/30* (2013.01); *C07K 2319/735* (2013.01); *C12N 2710/20022* (2013.01); *C12N 2710/20034* (2013.01); *C12N 2710/20071* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 6,306,397 B1 | 10/2001 | Edwards et al. | |
| 7,223,408 B2 * | 5/2007 | Cassetti | A61K 38/162 424/192.1 |
| 2008/0102084 A1 | 5/2008 | Wu et al. | |

FOREIGN PATENT DOCUMENTS

| | | |
|---|---|---|
| WO | WO 92/16636 A1 | 10/1992 |
| WO | WO 2004/030636 A2 | 4/2004 |
| WO | WO 2004/076489 A1 | 9/2004 |
| WO | WO 2005/089792 A1 | 9/2005 |
| WO | WO 2011/161244 A1 | 12/2011 |

OTHER PUBLICATIONS

Kim et al. Enhanced immunogenicity of human papillomavirus 16 L1 genetic vaccines fused to an ER-targeting secretory signal peptide and RANTES. Gene Ther. Aug. 2003;10(15):1268-73.*
GenBank: AAP36497.1 Homo sapiens chemokine (C-C motif) ligand 3, partial [synthetic construct]. Dated May 13, 2003.*
Fredriksen et al. Chemokine-idiotype fusion DNA vaccines are potentiated by bivalency and xenogeneic sequences. Blood. Sep. 15, 2007;110(6):1797-805. Epub May 31, 2007.*
Cheung et al. Plasmid encoding papillomavirus Type 16 (HPV16) DNA constructed with codon optimization improved the immunogenicity against HPV infection. Vaccine. Dec. 16, 2004;23(5):629-38.*
Huang et al. DNA vaccine encoding heat shock protein 60 co-linked to HPV16 E6 and E7 tumor antigens generates more potent immunotherapeutic effects than respective E6 or E7 tumor antigens. Gynecol Oncol. Dec. 2007;107(3):404-12. Epub Oct. 1, 2007.*
Drew et al. The human IgG3 hinge mediates the formation of antigen dimers that enhance humoral immune responses to DNA immunisation. Vaccine. Jul. 20, 2001;19(30):4115-20.*
NP_041326.1. transforming protein E7 [Human papillomavirus type 16]. Oct. 27, 2010.*
NP_041325.1. transforming protein E6 [Human papillomavirus type 16]. Oct. 27, 2010.*
Ristriani et al. A single-codon mutation converts HPV16 E6 oncoprotein into a potential tumor suppressor, which induces p53-dependent senescence of HPV-positive HeLa cervical cancer cells. Oncogene (2009) 28, 762-772.*

(Continued)

*Primary Examiner* — Nianxiang Zou
(74) *Attorney, Agent, or Firm* — Womble Bond Dickinson (US) LLP

(57) ABSTRACT

The present invention relates to therapeutic compounds, such as vaccines against human papillomavirus (HPV) and in particular to DNA vaccines against HPV16 or HPV18. The invention further relates to protein construct encoding homodimeric peptides, which peptides may be released from a DNA vaccine or used separately. Further described are pharmaceutical formulations, host cells and methods for producing the vaccines, as well as methods for the treatment of various HPV induced diseases, such as cancers and infectious diseases by application.

22 Claims, 5 Drawing Sheets

(56) References Cited

OTHER PUBLICATIONS

Figure 1:
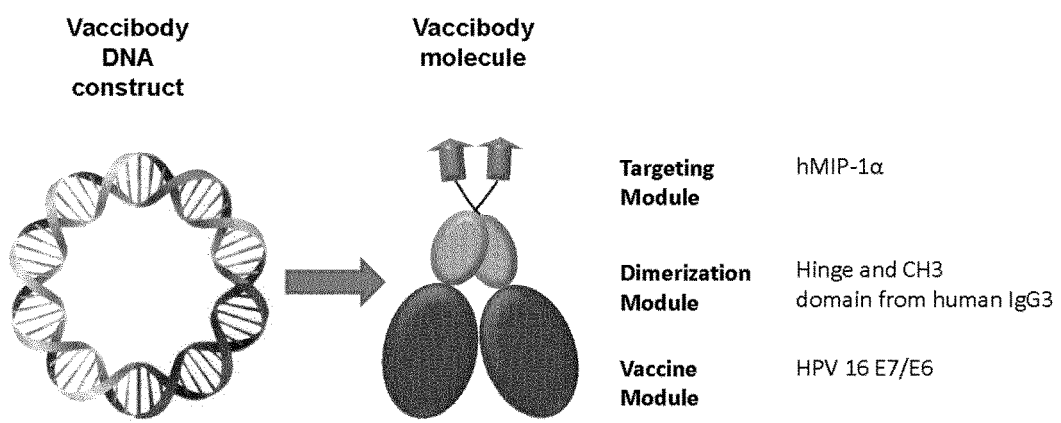

Nguyen et al. A mutant of human papillomavirus type 16 E6 deficient in binding alpha-helix partners displays reduced oncogenic potential in vivo. J Virol. Dec. 2002;76(24):13039-48.*
Dong et al. Determination of the binding affinity of different human papillomavirus E7 proteins for the tumour suppressor pRb by a plate-binding assay. J Virol Methods. Oct. 2001;98(1):91-8.*
Crook, T. et al., "Degradation of p53 Can Be Targeted by HPV E6 Sequences Distinct from Those Required for p53 Binding and Trans-Activation", *Cell*, Nov. 1, 1991, vol. 67, pp. 547-556, Cell Press.
Dalal, S., et al., "Mutational Analysis of Human Papillomavirus Type 16 E6 Demonstrates that p53 Degradation Is Necessary for Immortalization of Mammary Epithelial Cells", *Journal of Virology*, Feb. 1996, pp. 683-688, American Society for Microbiology.
Fredriksen, A.B., et al., "Chemokine-idiotype fusion DNA vaccines are potentiated by bivalency and xenogeneic sequences," *Blood*, Sep. 15, 2007. vol. 110, No. 6, pp. 1797-1805, The American Society of Hematology.
Fredriksen, A.B., et al., "DNA Vaccines Increase Immunogenicity of Idiotypic Tumor Antigen by Targeting Novel Fusion Proteins to Antigen-Presenting Cells," *Molecular Therapy*, 2006, vol. 13(4), pp. 776-785, The American Society of Gene Therapy.
Frøland, M., et al., "Targeted idiotype-fusion DNA vaccines for human multiple myeloma: preclinical testing," 2011, *European Journal of Haematology*, vol. 86, pp. 385-395, John Wiley & Sons A/S.
Mesplède, T., et al., "p53 Degradation Activity, Expression, and Subcellular Localization of E6 Proteins from 29 Human Papillomavirus Genotypes", *Journal of Virology*, Oct. 2011, vol. 86, No. 1, pp. 94-107.
Moody, C.A., et al., "Human papillomavirus oncoproteins: pathways to transformation", *Nature Reviews Cancer*, Aug. 2010, vol. 10, pp. 550-560, Macmillan Publishers Limited.
Münger, K., et al., "Complex formation of human papillomavirus E7 proteins with the retinoblastoma tumor suppressor gene product", *The EMBO Journal*, 1989, vol. 8, No. 13, pp. 4099-4105.
Münger, K., et al., "E6 Alignments HPV Compendium", Sep. 1997, 24 pages.
Münger, K., et al., "E7 Alignments HPV Compendium", Sep. 1997, 22 pages.
Nakagawa, S., et al., "Mutational Analysis of Human Papillomavirus Type 16 E6 Protein: Transforming Function for Human Cells and Degradation of p53 in Vitro", *Virology*, 1995, vol. 212, pp. 535-542, Academic Press, Inc.
Nguyen, M., et al., "A Mutant of Human Papillomavirus Type 16 E6 Deficient in Binding α-Helix Partners Displays Reduced Oncogenic Potential In Vivo", *Journal of Virology*, Dec. 2002, vol. 76, No. 24, pp. 13039-13048, American Society for Microbiology.
Nomine, Y., et al., "Structural and Functional Analysis of E6 Oncoprotein: Insights in the Molecular Pathways of Human Papillomavirus-Mediated Pathogenesis", *Molecular Cell*, Mar. 3, 2006, vol. 21, pp. 665-678, Elsevier Inc.
Øynebråten, I., et al., "P19-39. Vaccibodies: a novel vaccine strategy for HIV that target viral antigens to APC (Poster Presentation)," *Retrovirology*, Oct. 22, 2009, vol. 6, Suppl. 3, p. 359, BioMed Central Ltd.
Poláková, I., et al., "DNA vaccine against human papillomavirus type 16: Modifications of E6 oncogene", *Vaccine*, 2010, vol. 28, pp. 1506-1513, Elsevier, Ltd.
Ruffini, P.A., et al., "Human chemokine MIP1α increases efficiency of targeted DNA fusion vaccines," *Vaccine*, 2011, vol. 29, pp. 191-199, Elsevier Ltd.
Tunheim, G. et al., "Human receptors of innate immunity (CD14, TLR2) are promising targets for novel recombinant immunoglobulin-based vaccine candidates," *Vaccine*, 2007, vol. 25, pp. 4723-4734, Elsevier Ltd.
Xie, Q., et al., "Transforming Activity of a Novel Mutant of HPV16 E6E7 Fusion Gene", *Virologica Sinica*, Jun. 2011, vol. 26, No. 3, pp. 206-213, Springer-Verlang.
International Searching Authority, International Search Report and Written Opinion for International Application No. PCT/EP2012/076404, dated Mar. 25, 2013, 16 pages, European Patent Office, The Netherlands.
Gulliver, G., et al., "Both Conserved Region 1 (CR1) and CR2 of the Human Papillomavirus Type 16 E7 Oncogene Are Required for Induction of Epidermal Hyperplasia and Tumor Formation in Transgenic Mice," *Journal of Virology*, 1997, vol. 71(8), pp. 5905-5914.
Horwell, David C., "The 'peptoid approach to the design of non-peptide small molecule agonists and antagonists of neuropeptides," *TIBTECH*, 1995, vol. 13, pp. 132-134.
Knappscog, S., et al., "The level of synthesis and secretion of *Gaussia princeps* luciferase in transfected CHO cells is heavily dependent on the choice of signal peptide," *Journal of Biotechnology*, 2007, vol. 128, pp. 705-715.
Martoglio, B., et al., "Signal sequences: more than just greasy peptides", *trends in Cell Biology*, 1998, vol. 8, pp. 410-415.
Phelps, W., et al., "Structure-Function Analysis of the Human Papillomavirus Type 16 E7 Oncoprotein," *Journal of Virology*, 1992, vol. 66(4), pp. 2418-2427.
Simon, R., et al, "Peptoids: A modular approach to drug discovery," *Proc. Natl. Acad. Sci. USA*, 1992, vol. 89, pp. 9367-9371.

* cited by examiner

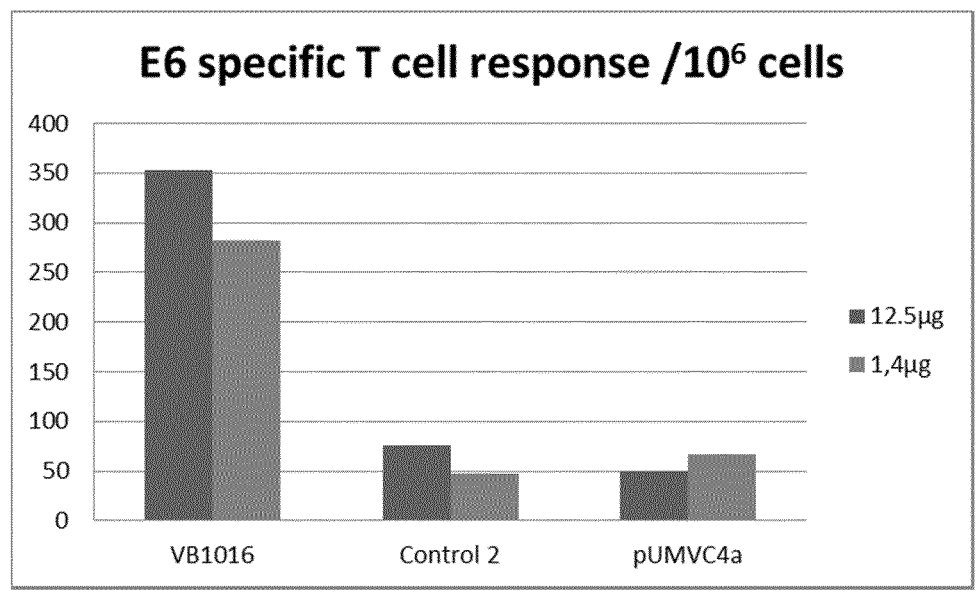
Fig. 3C
Figure 4:
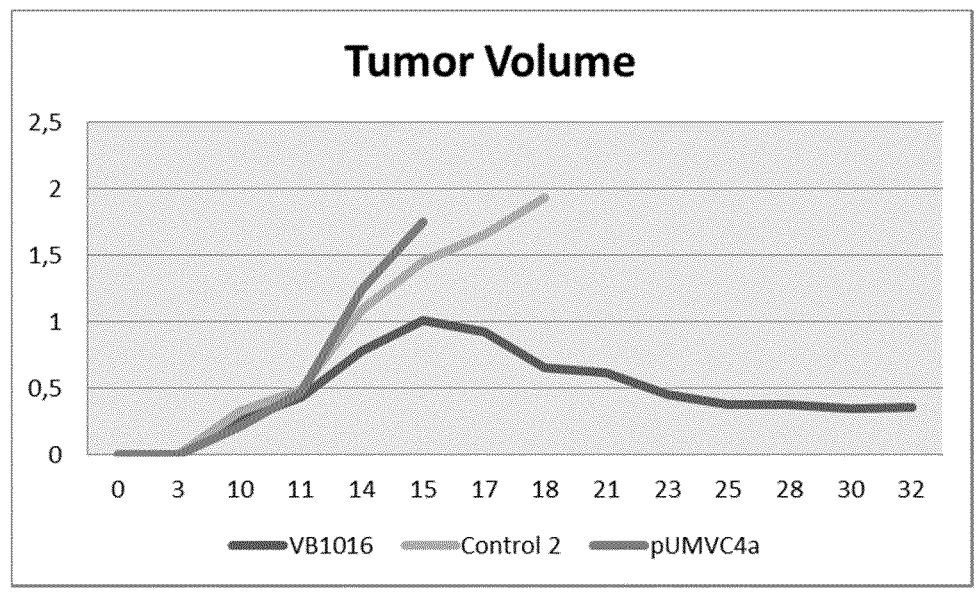

SEQUENCE LISTING

<160> NUMBER OF SEQ ID NOS: 34

<210> SEQ ID NO 1
<211> LENGTH: 93
<212> TYPE: PRT
<213> ORGANISM: Artificial
<220> FEATURE:
<223> OTHER INFORMATION: Synthetic

<400> SEQUENCE: 1

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90

<210> SEQ ID NO 2
<211> LENGTH: 1182
<212> TYPE: DNA
<213> ORGANISM: Artificial
<220> FEATURE:
<223> OTHER INFORMATION: Synthetic

<400> SEQUENCE: 2
atgcaggtct ccactgctgc ccttgccgtc ctcctctgca ccatggctct ctgcaaccag     60
gtcctctctg caccacttgc tgctgacacg ccgaccgcct gctgcttcag ctacacctcc    120
cgacagattc cacagaattt catagctgac tactttgaga cgagcagcca gtgctccaag    180
cccagtgtca tcttcctaac caagagaggc cggcaggtct gtgctgaccc cagtgaggag    240
tgggtccaga aatacgtcag tgacctggag ctgagtgccg agctcaaaac cccacttggt    300

```
gacacaactc acacagagcc caaatcttgt gacacacctc ccccgtgccc aaggtgccca      360
ggcggtggaa gcagcggagg tggaagtgga ggacagcccc gagaaccaca ggtgtacacc      420
ctgcccccat cccgggagga gatgaccaag aaccaggtca gcctgacctg cctggtcaaa      480
ggcttctacc ccagcgacat cgccgtggag tgggagagca gcgggcagcc ggagaacaac      540
tacaacacca cgcctcccat gctggactcc gacggctcct tcttcctcta cagcaagctc      600
accgtggaca agagcaggtg gcagcagggg aacatcttct catgctccgt gatgcatgag      660
gctctgcaca accgcttcac gcagaagagc ctctccctgt ctccgggtaa aggcctcggt      720
ggcctgatgt ttcaggaccc acaggagcga cccagaaagt taccacagtt atgcacagag      780
ctgcaaacaa ctatacatga tataatatta gaatgtgtgt actgcaagca acagttactg      840
cgacgtgagg tatatgactt tgcttttcgg gatttatgca tagtatatag agatgggaat      900
ccatatgctg tatgtgataa atgtttaaag ttttattcta aaattagtga gtatagacat      960
tattgttata gtttgtatgg aacaacatta gaacagcaat acaacaaacc gttgtgtgat     1020
ttgttaatta ggtgtattaa ctgtcaaaag ccactgtgtc ctgaagaaaa gcaaagacat     1080
ctggacaaaa agcaaagatt ccataatata aggggtcggt ggaccggtcg atgtatgtct     1140
tgttgcagat catcaagaac acgtagagaa acccagctgt aa                        1182
```

<210> SEQ ID NO 3
<211> LENGTH: 393
<212> TYPE: PRT
<213> ORGANISM: Artificial
<220> FEATURE:
<223> OTHER INFORMATION: Synthetic

<400> SEQUENCE: 3

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205
```

```
Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met Phe Gln Asp Pro Gln Glu Arg Pro Arg Lys Leu Pro Gln
                245                 250                 255

Leu Cys Thr Glu Leu Gln Thr Thr Ile His Asp Ile Ile Leu Glu Cys
            260                 265                 270

Val Tyr Cys Lys Gln Gln Leu Leu Arg Arg Glu Val Tyr Asp Phe Ala
        275                 280                 285

Phe Arg Asp Leu Cys Ile Val Tyr Arg Asp Gly Asn Pro Tyr Ala Val
    290                 295                 300

Cys Asp Lys Cys Leu Lys Phe Tyr Ser Lys Ile Ser Glu Tyr Arg His
305                 310                 315                 320

Tyr Cys Tyr Ser Leu Tyr Gly Thr Thr Leu Glu Gln Gln Tyr Asn Lys
                325                 330                 335

Pro Leu Cys Asp Leu Leu Ile Arg Cys Ile Asn Cys Gln Lys Pro Leu
            340                 345                 350

Cys Pro Glu Glu Lys Gln Arg His Leu Asp Lys Lys Gln Arg Phe His
        355                 360                 365

Asn Ile Arg Gly Arg Trp Thr Gly Arg Cys Met Ser Cys Cys Arg Ser
    370                 375                 380

Ser Arg Thr Arg Arg Glu Thr Gln Leu
385                 390

<210> SEQ ID NO 4
<211> LENGTH: 1182
<212> TYPE: DNA
<213> ORGANISM: Artificial
<220> FEATURE:
<223> OTHER INFORMATION: Synthetic

<400> SEQUENCE: 4
atgcaggtct ccactgctgc ccttgccgtc ctcctctgca ccatggctct ctgcaaccag      60
gtcctctctg caccacttgc tgctgacacg ccgaccgcct gctgcttcag ctacacctcc     120
cgacagattc cacagaattt catagctgac tactttgaga cgagcagcca gtgctccaag     180
cccagtgtca tcttcctaac caagagaggc cggcaggtct gtgctgaccc cagtgaggag     240
tgggtccaga atacgtcag tgacctggag ctgagtgccg agctcaaaac cccacttggt     300
gacacaactc acacagagcc aaatcttgt gacacacctc cccgtgccc aaggtgccca     360
ggcggtggaa gcagcggagg tggaagtgga ggacagcccc gagaaccaca ggtgtacacc     420
ctgccccat cccggggagga gatgaccaag aaccaggtca gcctgacctg cctggtcaaa     480
ggcttctacc ccagcgacat cgccgtggag tgggagagca cgggcagcc ggagaacaac     540
tacaacacca cgcctcccat gctggactcc gacggctcct tcttcctcta cagcaagctc     600
accgtggaca agagcaggtg gcagcagggg aacatcttct catgctccgt gatgcatgag     660
gctctgcaca accgcttcac gcagaagagc ctctccctgt ctccgggtaa aggcctcggt     720
ggcctgatgt ttcaggaccc acaggagcga cccagaaagt taccacagtt atgcacagag     780
ctgcaaacaa ctatacatga tataatatta gaatgtgtgt actgcaagca acagttactg     840
cgacgtgagg tatatgactt tgcttttcgg gatttatgca tagtatatag agatgggaat     900
ccatatgctg tacgagataa atgttaaag ttttattcta aaattagtga gtatagacat     960
tattgttata gtttgtatgg aacaacatta gaacagcaat acaacaaacc gttgtgtgat    1020
```

```
ttgttaatta ggtgtattaa ctgtcaaaag ccactgtgtc ctgaagaaaa gcaaagacat   1080
ctggacaaaa agcaaagatt ccataatata agggtcggt ggaccggtcg atgtatgtct   1140
tgttgcagat catcaagaac acgtagagaa acccagctgt aa                     1182
```

<210> SEQ ID NO 5
<211> LENGTH: 393
<212> TYPE: PRT
<213> ORGANISM: Artificial
<220> FEATURE:
<223> OTHER INFORMATION: Synthetic

<400> SEQUENCE: 5

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met Phe Gln Asp Pro Gln Glu Arg Pro Arg Lys Leu Pro Gln
                245                 250                 255

Leu Cys Thr Glu Leu Gln Thr Thr Ile His Asp Ile Leu Glu Cys
            260                 265                 270

Val Tyr Cys Lys Gln Gln Leu Leu Arg Arg Glu Val Tyr Asp Phe Ala
    275                 280                 285

Phe Arg Asp Leu Cys Ile Val Tyr Arg Asp Gly Asn Pro Tyr Ala Val
    290                 295                 300

Arg Asp Lys Cys Leu Lys Phe Tyr Ser Lys Ile Ser Glu Tyr Arg His
305                 310                 315                 320

Tyr Cys Tyr Ser Leu Tyr Gly Thr Thr Leu Glu Gln Gln Tyr Asn Lys
                325                 330                 335
```

Pro Leu Cys Asp Leu Leu Ile Arg Cys Ile Asn Cys Gln Lys Pro Leu
            340                 345                 350

Cys Pro Glu Glu Lys Gln Arg His Leu Asp Lys Lys Gln Arg Phe His
            355                 360                 365

Asn Ile Arg Gly Arg Trp Thr Gly Arg Cys Met Ser Cys Cys Arg Ser
        370                 375                 380

Ser Arg Thr Arg Arg Glu Thr Gln Leu
385                 390

<210> SEQ ID NO 6
<211> LENGTH: 1182
<212> TYPE: DNA
<213> ORGANISM: Artificial
<220> FEATURE:
<223> OTHER INFORMATION: Synthetic

<400> SEQUENCE: 6
atgcaggtct ccactgctgc ccttgccgtc ctcctctgca ccatggctct ctgcaaccag      60
gtcctctctg caccacttgc tgctgacacg ccgaccgcct gctgcttcag ctacacctcc     120
cgacagattc cacagaattt catagctgac tactttgaga cgagcagcca gtgctccaag     180
cccagtgtca tcttcctaac caagagaggc cggcaggtct gtgctgaccc cagtgaggag     240
tgggtccaga atacgtcag tgacctggag ctgagtgccg agctcaaaac ccccacttggt     300
gacacaactc acacagagcc caatcttgt gacacacctc cccgtgccc aaggtgccca     360
ggcggtggaa gcagcggagg tggaagtgga ggacagcccc gagaaccaca ggtgtacacc     420
ctgccccat cccgggagga gatgaccaag aaccaggtca gcctgacctg cctggtcaaa     480
ggcttctacc ccagcgacat cgccgtggag tgggagagca cgggcagcc ggagaacaac     540
tacaacacca cgcctcccat gctggactcc gacggctcct tcttcctcta cagcaagctc     600
accgtggaca gagcaggtg gcagcagggg aacatcttct catgctccgt gatgcatgag     660
gctctgcaca accgcttcac gcagaagagc ctctccctgt ctccgggtaa aggcctcggt     720
ggcctgatgt tcaggaccc acaggagcga cccagaaagt taccacagtt atgcacagag     780
ctgcaaacaa ctatacatga tataatatta gaatgtgtgt actgcaagca acagttactg     840
cgacgtgagg tatatgactt tgcttttcgg gatttatgca agtatatag agatgggaat     900
ccatatgctg tatgtgataa atgtttaaag ttttattcta aaattagtga gtatagacat     960
tattgttata gttttgtatgg aacaacatta gaacagcaat acaacaaacc gttgtgtgat    1020
ttgttaatta gtgtattaa ccgacaaaag ccactgtgtc ctgaagaaaa gcaaagacat    1080
ctggacaaaa agcaaagatt ccataatata aggggtcggt ggaccggtcg atgtatgtct    1140
tgttgcagat catcaagaac acgtagagaa acccagctgt aa                       1182

<210> SEQ ID NO 7
<211> LENGTH: 393
<212> TYPE: PRT
<213> ORGANISM: Artificial
<220> FEATURE:
<223> OTHER INFORMATION: Synthetic

<400> SEQUENCE: 7

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
 50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
        115                 120                 125

Ser Gly Gly Gln Pro Arg Glu Pro Gln Val Tyr Thr Leu Pro Pro Ser
130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
210                 215                 220

Arg Phe Thr Gln Lys Ser Leu Ser Leu Ser Pro Gly Lys Gly Leu Gly
225                 230                 235                 240

Gly Leu Met Phe Gln Asp Pro Gln Glu Arg Pro Arg Lys Leu Pro Gln
                245                 250                 255

Leu Cys Thr Glu Leu Gln Thr Thr Ile His Asp Ile Ile Leu Glu Cys
            260                 265                 270

Val Tyr Cys Lys Gln Gln Leu Leu Arg Arg Glu Val Tyr Asp Phe Ala
        275                 280                 285

Phe Arg Asp Leu Cys Ile Val Tyr Arg Asp Gly Asn Pro Tyr Ala Val
290                 295                 300

Cys Asp Lys Cys Leu Lys Phe Tyr Ser Lys Ile Ser Glu Tyr Arg His
305                 310                 315                 320

Tyr Cys Tyr Ser Leu Tyr Gly Thr Thr Leu Glu Gln Gln Tyr Asn Lys
                325                 330                 335

Pro Leu Cys Asp Leu Leu Ile Arg Cys Ile Asn Arg Gln Lys Pro Leu
            340                 345                 350

Cys Pro Glu Glu Lys Gln Arg His Leu Asp Lys Lys Gln Arg Phe His
        355                 360                 365

Asn Ile Arg Gly Arg Trp Thr Gly Arg Cys Met Ser Cys Cys Arg Ser
370                 375                 380

Ser Arg Thr Arg Arg Glu Thr Gln Leu
385                 390

<210> SEQ ID NO 8
<211> LENGTH: 1182
<212> TYPE: DNA
<213> ORGANISM: Artificial
<220> FEATURE:
<223> OTHER INFORMATION: Synthetic

<400> SEQUENCE: 8

```
atgcaggtct ccactgctgc ccttgccgtc ctcctctgca ccatggctct ctgcaaccag     60
gtcctctctg caccacttgc tgctgacacg ccgaccgcct gctgcttcag ctacacctcc    120
cgacagattc cacagaattt catagctgac tactttgaga cgagcagcca gtgctccaag    180
cccagtgtca tcttcctaac caagagaggc cggcaggtct gtgctgaccc cagtgaggag    240
tgggtccaga atacgtcag tgacctggag ctgagtgccg agctcaaaac cccacttggt    300
gacacaactc acacagagcc caaatcttgt gacacacctc cccgtgccc aaggtgccca    360
ggcggtggaa gcagcggagg tggaagtgga ggacagcccc gagaaccaca ggtgtacacc    420
ctgcccccat cccgggagga gatgaccaag aaccaggtca gcctgacctg cctggtcaaa    480
ggcttctacc ccagcgacat cgccgtggag tgggagagca gcgggcagcc ggagaacaac    540
tacaacacca cgcctcccat gctggactcc gacggctcct tcttcctcta cagcaagctc    600
accgtggaca agagcaggtg gcagcagggg aacatcttct catgctccgt gatgcatgag    660
gctctgcaca accgcttcac gcagaagagc ctctccctgt ctccgggtaa aggcctcggt    720
ggcctgatgt ttcaggaccc acaggagcga cccagaaagt taccacagtt atgcacagag    780
ctgcaaacaa ctatacatga tataatatta gaatgtgtgt actgcaagca acagttactg    840
cgacgtgagg tatatgactt tgctcgacgg gatttatgca tagtatatag agatgggaat    900
ccatatgctg tacgagataa atgtttaaag ttttattcta aaattagtga gtatagacat    960
tattgttata gtttgtatgg aacaacatta gaacagcaat acaacaaacc gttgtgtgat   1020
ttgttaatta ggtgtattaa ccgacaaaag ccactgtgtc ctgaagaaaa gcaaagacat   1080
ctggacaaaa agcaaagatt ccataatata aggggtcggt ggaccggtcg atgtatgtct   1140
tgttgcagat catcaagaac acgtagagaa acccagctgt aa                      1182
```

<210> SEQ ID NO 9
<211> LENGTH: 393
<212> TYPE: PRT
<213> ORGANISM: Artificial
<220> FEATURE:
<223> OTHER INFORMATION: Synthetic

<400> SEQUENCE: 9

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160
```

```
Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met Phe Gln Asp Pro Gln Glu Arg Pro Arg Lys Leu Pro Gln
                245                 250                 255

Leu Cys Thr Glu Leu Gln Thr Thr Ile His Asp Ile Ile Leu Glu Cys
            260                 265                 270

Val Tyr Cys Lys Gln Gln Leu Leu Arg Arg Glu Val Tyr Asp Phe Ala
        275                 280                 285

Arg Arg Asp Leu Cys Ile Val Tyr Arg Asp Gly Asn Pro Tyr Ala Val
    290                 295                 300

Arg Asp Lys Cys Leu Lys Phe Tyr Ser Lys Ile Ser Glu Tyr Arg His
305                 310                 315                 320

Tyr Cys Tyr Ser Leu Tyr Gly Thr Thr Leu Glu Gln Gln Tyr Asn Lys
                325                 330                 335

Pro Leu Cys Asp Leu Leu Ile Arg Cys Ile Asn Arg Gln Lys Pro Leu
            340                 345                 350

Cys Pro Glu Glu Lys Gln Arg His Leu Asp Lys Lys Gln Arg Phe His
        355                 360                 365

Asn Ile Arg Gly Arg Trp Thr Gly Arg Cys Met Ser Cys Cys Arg Ser
    370                 375                 380

Ser Arg Thr Arg Arg Glu Thr Gln Leu
385                 390

<210> SEQ ID NO 10
<211> LENGTH: 1023
<212> TYPE: DNA
<213> ORGANISM: Artificial
<220> FEATURE:
<223> OTHER INFORMATION: Synthetic

<400> SEQUENCE: 10
atgcaggtct ccactgctgc ccttgccgtc ctcctctgca ccatggctct ctgcaaccag      60
gtcctctctg caccacttgc tgctgacacg ccgaccgcct gctgcttcag ctacacctcc     120
cgacagattc acagaatttt catagctgac tactttgaga cgagcagcca gtgctccaag     180
cccagtgtca tcttcctaac caagagaggc cggcaggtct gtgctgaccc cagtgaggag     240
tgggtccaga aatacgtcag tgacctggag ctgagtgccg agctcaaaac cccacttggt     300
gacacaactc acacagagcc caatcttgt gacacacctc ccccgtgccc aaggtgccca     360
ggcggtggaa gcagcggagg tggaagtgga ggacagcccc gagaaccaca ggtgtacacc     420
ctgcccccat cccgggagga gatgaccaag aaccaggtca gcctgacctg cctggtcaaa     480
ggcttctacc ccagcgacat cgccgtggag tgggagagca cgggcagcc ggagaacaac     540 tacaacacca cgcctcccat gctggactcc gacggctcct tcttcctcta cagcaagctc     600
accgtggaca agagcaggtg gcagcagggg aacatcttct catgctccgt gatgcatgag     660
gctctgcaca accgcttcac gcagaagagc ctctcccctgt ctccgggtaa aggcctcggt     720
```

-continued

```
ggcctgatgc atggagatac acctacattg catgaatata tgttagattt gcaaccagag    780
acaactgatc tctactgtta tgagcaatta aatgacagct cagaggagga ggatgaaata    840
gatggtccag ctggacaagc agaaccggac agagcccatt acaatattgt aacctttgt    900 tgcaagtgtg actctacgct tcggttgtgc gtacaaagca cacacgtaga cattcgtact    960
ttggaagacc tgttaatggg cacactagga attgtgtgcc ccatctgttc tcagaaacca   1020
taa                                                                 1023
```

<210> SEQ ID NO 11
<211> LENGTH: 340
<212> TYPE: PRT
<213> ORGANISM: Artificial
<220> FEATURE:
<223> OTHER INFORMATION: Synthetic

<400> SEQUENCE: 11

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
                245                 250                 255

Leu Gln Pro Glu Thr Thr Asp Leu Tyr Cys Tyr Glu Gln Leu Asn Asp
            260                 265                 270

Ser Ser Glu Glu Glu Asp Glu Ile Asp Gly Pro Ala Gly Gln Ala Glu
        275                 280                 285

Pro Asp Arg Ala His Tyr Asn Ile Val Thr Phe Cys Cys Lys Cys Asp
    290                 295                 300
```

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Cys Pro Ile Cys
            325                 330                 335

Ser Gln Lys Pro
        340

<210> SEQ ID NO 12
<211> LENGTH: 1023
<212> TYPE: DNA
<213> ORGANISM: Artificial
<220> FEATURE:
<223> OTHER INFORMATION: Synthetic

<400> SEQUENCE: 12

| | | | | | |
|---|---|---|---|---|---|
| atgcaggtct | ccactgctgc | ccttgccgtc | ctcctctgca | ccatggctct | ctgcaaccag | 60 |
| gtcctctctg | caccacttgc | tgctgacacg | ccgaccgcct | gctgcttcag | ctacacctcc | 120 |
| cgacagattc | cacagaattt | catagctgac | tactttgaga | cgagcagcca | gtgctccaag | 180 |
| cccagtgtca | tcttcctaac | caagagaggc | cggcaggtct | gtgctgaccc | cagtgaggag | 240 |
| tgggtccaga | atacgtcag | tgacctggag | ctgagtgccg | agctcaaaac | cccacttggt | 300 |
| gacacaactc | acacagagcc | caaatcttgt | gacacacctc | ccccgtgccc | aaggtgccca | 360 |
| ggcggtggaa | gcagcggagg | tggaagtgga | ggacagcccc | gagaaccaca | ggtgtacacc | 420 |
| ctgccccat | cccgggagga | gatgaccaag | aaccaggtca | gcctgacctg | cctggtcaaa | 480 |
| ggcttctacc | ccagcgacat | cgccgtggag | tgggagagca | gcgggcagcc | ggagaacaac | 540 |
| tacaacacca | cgcctcccat | gctggactcc | gacggctcct | tcttcctcta | cagcaagctc | 600 |
| accgtggaca | agagcaggtg | gcagcagggg | aacatcttct | catgctccgt | gatgcatgag | 660 |
| gctctgcaca | accgcttcac | gcagaagagc | ctctccctgt | ctccgggtaa | aggcctcggt | 720 |
| ggcctgatgc | atggagatac | acctacattg | catgaatata | tgttagattt | gcaaccagag | 780 |
| acaactgatc | tctacggata | tggacaatta | aatgacagct | cagaggagga | ggatgaaata | 840 |
| gatggtccag | ctggacaagc | agaaccggac | agagcccatt | acaatattgt | aaccttttgt | 900 |
| tgcaagtgtg | actctacgct | tcggttgtgc | gtacaaagca | cacgtaga | cattcgtact | 960 |
| ttggaagacc | tgttaatggg | cacactagga | attgtgtgcc | ccatctgttc | tcagaaacca | 1020 |
| taa | | | | | | 1023 |

<210> SEQ ID NO 13
<211> LENGTH: 340
<212> TYPE: PRT
<213> ORGANISM: Artificial
<220> FEATURE:
<223> OTHER INFORMATION: Synthetic

<400> SEQUENCE: 13

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu

```
                65                  70                  75                  80
        Trp Val Gln Lys Tyr Val Ser Asp Leu Glu Leu Ser Ala Glu Leu Lys
                        85                  90                  95

Thr Pro Leu Gly Asp Thr Thr His Thr Glu Pro Lys Ser Cys Asp Thr
                    100                 105                 110

Pro Pro Pro Cys Pro Arg Cys Pro Gly Gly Ser Ser Gly Gly Gly
                115                 120                 125

Ser Gly Gly Gln Pro Arg Glu Pro Gln Val Tyr Thr Leu Pro Pro Ser
            130                 135                 140

Arg Glu Glu Met Thr Lys Asn Gln Val Ser Leu Thr Cys Leu Val Lys
        145                 150                 155                 160

Gly Phe Tyr Pro Ser Asp Ile Ala Val Glu Trp Glu Ser Ser Gly Gln
                        165                 170                 175

Pro Glu Asn Asn Tyr Asn Thr Thr Pro Pro Met Leu Asp Ser Asp Gly
                    180                 185                 190

Ser Phe Phe Leu Tyr Ser Lys Leu Thr Val Asp Lys Ser Arg Trp Gln
                195                 200                 205

Gln Gly Asn Ile Phe Ser Cys Ser Val Met His Glu Ala Leu His Asn
            210                 215                 220

Arg Phe Thr Gln Lys Ser Leu Ser Leu Ser Pro Gly Lys Gly Leu Gly
        225                 230                 235                 240

Gly Leu Met His Gly Asp Thr Pro Thr Leu His Glu Tyr Met Leu Asp
                        245                 250                 255

Leu Gln Pro Glu Thr Thr Asp Leu Tyr Gly Tyr Gly Gln Leu Asn Asp
                    260                 265                 270

Ser Ser Glu Glu Glu Asp Glu Ile Asp Gly Pro Ala Gly Gln Ala Glu
                275                 280                 285

Pro Asp Arg Ala His Tyr Asn Ile Val Thr Phe Cys Cys Lys Cys Asp
            290                 295                 300

Ser Thr Leu Arg Leu Cys Val Gln Ser Thr His Val Asp Ile Arg Thr
        305                 310                 315                 320

Leu Glu Asp Leu Leu Met Gly Thr Leu Gly Ile Val Cys Pro Ile Cys
                        325                 330                 335

Ser Gln Lys Pro
                    340

<210> SEQ ID NO 14
<211> LENGTH: 1023
<212> TYPE: DNA
<213> ORGANISM: Artificial
<220> FEATURE:
<223> OTHER INFORMATION: Synthetic

<400> SEQUENCE: 14
atgcaggtct ccactgctgc ccttgccgtc ctcctctgca ccatggctct ctgcaaccag      60
gtcctctctg caccacttgc tgctgacacg ccgaccgcct gctgcttcag ctacaccctcc   120 cgacagattc cacagaattt catagctgac tactttgaga cgagcagcca gtgctccaag   180
cccagtgtca tcttcctaac caagagaggc cggcaggtct gtgctgaccc cagtgaggag   240
tgggtccaga aatacgtcag tgacctggag ctgagtgccg agctcaaaac ccccacttggt  300 gacacaactc acacagagcc caaatcttgt gacacacctc cccgtgccc  aaggtgccca   360 ggcggtggaa gcagcggagg tggaagtgga ggacagcccc gagaaccaca ggtgtacacc   420
ctgcccccat cccgggagga gatgaccaag aaccaggtca gcctgacctg cctggtcaaa   480
```

-continued

```
ggcttctacc ccagcgacat cgccgtggag tgggagagca gcgggcagcc ggagaacaac      540
tacaacacca cgcctcccat gctggactcc gacggctcct tcttcctcta cagcaagctc      600
accgtggaca agagcaggtg gcagcagggg aacatcttct catgctccgt gatgcatgag      660
gctctgcaca accgcttcac gcagaagagc ctctccctgt ctccgggtaa aggcctcggt      720
ggcctgatgc atggagatac acctacattg catgaatata tgttagattt gcaaccagag      780
acaactgatc tctacggata tggacaatta aatgacagct cagaggagga ggatgaaata      840
gatggtccag ctggacaagc agaaccggac agagcccatt acaatattgt aacctttgga      900
tgcaagggag actctacgct tcggttgtgc gtacaaagca cacgtagaca cattcgtact      960
ttggaagacc tgttaatggg cacactagga attgtgtgcc ccatctgttc tcagaaacca     1020
taa                                                                  1023
```

<210> SEQ ID NO 15
<211> LENGTH: 340
<212> TYPE: PRT
<213> ORGANISM: Artificial
<220> FEATURE:
<223> OTHER INFORMATION: Synthetic

<400> SEQUENCE: 15

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
                245                 250                 255

Leu Gln Pro Glu Thr Thr Asp Leu Tyr Gly Tyr Gly Gln Leu Asn Asp
```

```
                    260                 265                 270
Ser Ser Glu Glu Glu Asp Glu Ile Asp Gly Pro Ala Gly Gln Ala Glu
            275                 280                 285

Pro Asp Arg Ala His Tyr Asn Ile Val Thr Phe Gly Cys Lys Gly Asp
        290                 295                 300

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Cys Pro Ile Cys
                325                 330                 335

Ser Gln Lys Pro
            340
```

<210> SEQ ID NO 16
<211> LENGTH: 1023
<212> TYPE: DNA
<213> ORGANISM: Artificial
<220> FEATURE:
<223> OTHER INFORMATION: Synthetic

<400> SEQUENCE: 16

```
atgcaggtct ccactgctgc ccttgccgtc ctcctctgca ccatggctct ctgcaaccag      60
gtcctctctg caccacttgc tgctgacacg ccgaccgcct gctgcttcag ctacacctcc     120
cgacagattc cacagaattt catagctgac tactttgaga cgagcagcca gtgctccaag     180
cccagtgtca tcttcctaac caagagaggc cggcaggtct gtgctgaccc cagtgaggag     240
tgggtccaga aatacgtcag tgacctggag ctgagtgccg agctcaaaac cccacttggt     300
gacacaactc acacagagcc caatcttgt gacacacctc cccgtgccc aaggtgccca      360
ggcggtggaa gcagcggagg tggaagtgga ggacagcccc gagaaccaca ggtgtacacc     420
ctgcccccat cccgggagga gatgaccaag aaccaggtca gcctgacctg cctggtcaaa     480
ggcttctacc ccagcgacat cgccgtggag tgggagagca gcgggcagcc ggagaacaac     540
tacaacacca cgcctcccat gctggactcc gacggctcct tcttcctcta cagcaagctc     600
accgtggaca gagcaggtg gcagcagggg aacatcttct catgctccgt gatgcatgag      660
gctctgcaca accgcttcac gcagaagagc ctctccctgt ctccgggtaa aggcctcggt     720
ggcctgatgc atggagatac acctacattg catgaatata tgttagattt gcaaccagag     780
acaactgatc tctacggata tggacaatta atgacagct cagaggagga ggatgaaata      840
gatggtccag ctggacaagc agaaccggac agagcccatt acaatattgt aacctttgt      900
tgcaagtgtg actctacgct tcggttgtgc gtacaaagca cacacgtaga cattcgtact     960
ttggaagacc tgttaatggg cacactagga attgtggac ccatcggatc tcagaaacca     1020
taa                                                                   1023
```

<210> SEQ ID NO 17
<211> LENGTH: 340
<212> TYPE: PRT
<213> ORGANISM: Artificial
<220> FEATURE:
<223> OTHER INFORMATION: Synthetic

<400> SEQUENCE: 17

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30
```

```
Ala Cys Cys Phe Ser Tyr Thr Ser Arg Gln Ile Pro Gln Asn Phe Ile
         35                  40                  45

Ala Asp Tyr Phe Glu Thr Ser Ser Gln Cys Ser Lys Pro Ser Val Ile
 50                  55                  60

Phe Leu Thr Lys Arg Gly Arg Gln Val Cys Ala Asp Pro Ser Glu Glu
 65                  70                  75                  80

Trp Val Gln Lys Tyr Val Ser Asp Leu Glu Leu Ser Ala Glu Leu Lys
                 85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
            115                 120                 125

Ser Gly Gly Gln Pro Arg Glu Pro Gln Val Tyr Thr Leu Pro Pro Ser
130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
                245                 250                 255

Leu Gln Pro Glu Thr Thr Asp Leu Tyr Gly Tyr Gly Gln Leu Asn Asp
            260                 265                 270

Ser Ser Glu Glu Glu Asp Glu Ile Asp Gly Pro Ala Gly Gln Ala Glu
        275                 280                 285

Pro Asp Arg Ala His Tyr Asn Ile Val Thr Phe Cys Cys Lys Cys Asp
    290                 295                 300

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Gly Pro Ile Gly
                325                 330                 335

Ser Gln Lys Pro
            340

<210> SEQ ID NO 18
<211> LENGTH: 1506
<212> TYPE: DNA
<213> ORGANISM: Artificial
<220> FEATURE:
<223> OTHER INFORMATION: Synthetic

<400> SEQUENCE: 18
atgcaggtct ccactgctgc ccttgccgtc ctcctctgca ccatggctct ctgcaaccag     60
gtcctctctg caccacttgc tgctgacacg ccgaccgcct gctgcttcag ctacacctcc    120
cgacagattc cacagaattt catagctgac tactttgaga cgagcagcca gtgctccaag    180
cccagtgtca tcttcctaac caagagaggc cggcaggtct gtgctgaccc cagtgaggag    240
tgggtccaga aatacgtcag tgacctggag ctgagtgccg agctcaaaac cccacttggt    300
```

```
gacacaactc acacagagcc caaatcttgt gacacacctc ccccgtgccc aaggtgccca    360
ggcggtggaa gcagcggagg tggaagtgga ggacagcccc gagaaccaca ggtgtacacc    420
ctgcccccat cccggagga gatgaccaag aaccaggtca gcctgacctg cctggtcaaa     480
ggcttctacc ccagcgacat cgccgtggag tgggagagca cgggcagcc ggagaacaac     540 tacaacacca cgcctcccat gctggactcc gacggctcct tcttcctcta cagcaagctc    600
accgtggaca gagcaggtg gcagcagggg aacatcttct catgctccgt gatgcatgag     660
gctctgcaca accgcttcac gcagaagagc ctctccctgt ctccgggtaa aggcctcggt    720
ggcctgatgc atgagatac acctacattg catgaatata tgttagattt gcaaccagag     780
acaactgatc tctacggata tggacaatta aatgacagct cagaggagga ggatgaaata    840
gatggtccag ctggacaagc agaaccggac agagcccatt acaatattgt aaccttttgt    900
tgcaagtgtg actctacgct tcggttgtgc gtacaaagca cacacgtaga cattcgtact    960
ttggaagacc tgttaatggg cacactagga attgtgtgcc ccatctgttc tcagaaacca    1020
ggcggtggaa gcagcggagg tggaagtgga atgtttcagg acccacagga gcgacccaga    1080
aagttaccac agttatgcac agagctgcaa acaactatac atgatataat attagaatgt    1140
gtgtactgca agcaacagtt actgcgacgt gaggtatatg actttgctcg acgggattta    1200
tgcatagtat atagagatgg gaatccatat gctgtacgag ataaatgttt aaagttttat    1260
tctaaaatta gtgagtatag acattattgt tatagtttgt atggaacaac attagaacag    1320
caatacaaca aaccgttgtg tgatttgtta attaggtgta ttaaccgaca aaagccactg    1380
tgtcctgaag aaaagcaaag acatctggac aaaaagcaaa gattccataa tataagggt    1440 cggtggaccg gtcgatgtat gtcttgttgc agatcatcaa gaacacgtag agaaacccag    1500
ctgtaa                                                             1506
```

<210> SEQ ID NO 19
<211> LENGTH: 501
<212> TYPE: PRT
<213> ORGANISM: Artificial
<220> FEATURE:
<223> OTHER INFORMATION: Synthetic

<400> SEQUENCE: 19

Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
            165                 170                 175

Pro Glu Asn Asn Tyr Asn Thr Thr Pro Pro Met Leu Asp Ser Asp Gly
        180                 185                 190

Ser Phe Phe Leu Tyr Ser Lys Leu Thr Val Asp Lys Ser Arg Trp Gln
    195                 200                 205

Gln Gly Asn Ile Phe Ser Cys Ser Val Met His Glu Ala Leu His Asn
210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
            245                 250                 255

Leu Gln Pro Glu Thr Thr Asp Leu Tyr Gly Tyr Gly Gln Leu Asn Asp
        260                 265                 270

Ser Ser Glu Glu Glu Asp Glu Ile Asp Gly Pro Ala Gly Gln Ala Glu
    275                 280                 285

Pro Asp Arg Ala His Tyr Asn Ile Val Thr Phe Cys Cys Lys Cys Asp
290                 295                 300

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Cys Pro Ile Cys
            325                 330                 335

Ser Gln Lys Pro Gly Gly Gly Ser Gly Gly Gly Ser Gly Met Phe
    340                 345                 350

Gln Asp Pro Gln Glu Arg Pro Arg Lys Leu Pro Gln Leu Cys Thr Glu
    355                 360                 365

Leu Gln Thr Thr Ile His Asp Ile Ile Leu Glu Cys Val Tyr Cys Lys
370                 375                 380

Gln Gln Leu Leu Arg Arg Glu Val Tyr Asp Phe Ala Arg Arg Asp Leu
385                 390                 395                 400

Cys Ile Val Tyr Arg Asp Gly Asn Pro Tyr Ala Val Arg Asp Lys Cys
            405                 410                 415

Leu Lys Phe Tyr Ser Lys Ile Ser Glu Tyr Arg His Tyr Cys Tyr Ser
        420                 425                 430

Leu Tyr Gly Thr Thr Leu Glu Gln Gln Tyr Asn Lys Pro Leu Cys Asp
    435                 440                 445

Leu Leu Ile Arg Cys Ile Asn Arg Gln Lys Pro Leu Cys Pro Glu Glu
    450                 455                 460

Lys Gln Arg His Leu Asp Lys Lys Gln Arg Phe His Asn Ile Arg Gly
465                 470                 475                 480

Arg Trp Thr Gly Arg Cys Met Ser Cys Cys Arg Ser Ser Arg Thr Arg
            485                 490                 495

Arg Glu Thr Gln Leu
            500

<210> SEQ ID NO 20
<211> LENGTH: 1506
<212> TYPE: DNA
<213> ORGANISM: Artificial
<220> FEATURE:
<223> OTHER INFORMATION: Synthetic

<400> SEQUENCE: 20

```
atgcaggtct ccactgctgc ccttgccgtc ctcctctgca ccatggctct ctgcaaccag      60
gtcctctctg caccacttgc tgctgacacg ccgaccgcct gctgcttcag ctacacctcc     120
cgacagattc cacagaattt catagctgac tactttgaga cgagcagcca gtgctccaag     180
cccagtgtca tcttcctaac caagagaggc cggcaggtct gtgctgaccc cagtgaggag     240
tgggtccaga atacgtcag tgacctggag ctgagtgccg agctcaaaac cccacttggt      300
gacacaactc acacagagcc caaatcttgt gacacacctc cccgtgccc aaggtgccca      360
ggcggtggaa gcagcggagg tggaagtgga ggacagcccc gagaaccaca ggtgtacacc     420
ctgcccccat cccgggagga gatgaccaag aaccaggtca gcctgacctg cctggtcaaa     480
ggcttctacc ccagcgacat cgccgtggag tgggagagca gcgggcagcc ggagaacaac     540
tacaacacca cgcctcccat gctggactcc gacggctcct tcttcctcta cagcaagctc     600
accgtggaca gagcaggtg gcagcagggg aacatcttct catgctccgt gatgcatgag      660
gctctgcaca accgcttcac gcagaagagc ctctccctgt ctccgggtaa aggcctcggt     720
ggcctgatgc atggagatac acctacattg catgaatata tgttagattt gcaaccagag     780
acaactgatc tctacggata tggacaatta aatgacagct cagaggagga ggatgaaata     840
gatggtccag ctggacaagc agaaccggac agagcccatt acaatattgt aacctttgt     900
tgcaagtgtg actctacgct tcggttgtgc gtacaaagca cacacgtaga cattcgtact    960
ttggaagacc tgttaatggg cacactagga attgtgtgcc ccatctgttc tcagaaacca    1020
ggcggtggaa gcagcggagg tggaagtgga atgtttcagg acccacagga gcgacccaga    1080
aagttaccac agttatgcac agagctgcaa acaactatac atgatataat attagaatgt    1140
gtgtactgca gcaacagtt actgcgacgt gaggtatatg actttgcttt tcgggattta    1200
tgcatagtat atagagatgg gaatccatat gctgtacgag ataaatgttt aaagttttat    1260
tctaaaatta gtgagtatag acattattgt tatagtttgt atggaacaac attagaacag    1320
caatacaaca aaccgttgtg tgatttgtta attaggtgta ttaaccgaca aaagccactg    1380
tgtcctgaag aaaagcaaag acatctggac aaaaagcaaa gattccataa tataaggggt    1440
cggtggaccg tcgatgtat gtcttgttgc agatcatcaa gaacacgtag agaaacccag    1500
ctgtaa                                                                1506
```

<210> SEQ ID NO 21
<211> LENGTH: 501
<212> TYPE: PRT
<213> ORGANISM: Artificial
<220> FEATURE:
<223> OTHER INFORMATION: Synthetic

<400> SEQUENCE: 21

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
```

```
                    85                  90                  95
Thr Pro Leu Gly Asp Thr Thr His Thr Glu Pro Lys Ser Cys Asp Thr
                100                 105                 110

Pro Pro Pro Cys Pro Arg Cys Pro Gly Gly Ser Ser Gly Gly Gly
            115                 120                 125

Ser Gly Gly Gln Pro Arg Glu Pro Gln Val Tyr Thr Leu Pro Pro Ser
            130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175

Pro Glu Asn Asn Tyr Asn Thr Thr Pro Pro Met Leu Asp Ser Asp Gly
                180                 185                 190

Ser Phe Phe Leu Tyr Ser Lys Leu Thr Val Asp Lys Ser Arg Trp Gln
                195                 200                 205

Gln Gly Asn Ile Phe Ser Cys Ser Val Met His Glu Ala Leu His Asn
            210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
                245                 250                 255

Leu Gln Pro Glu Thr Thr Asp Leu Tyr Gly Tyr Gly Gln Leu Asn Asp
                260                 265                 270

Ser Ser Glu Glu Glu Asp Glu Ile Asp Gly Pro Ala Gly Gln Ala Glu
            275                 280                 285

Pro Asp Arg Ala His Tyr Asn Ile Val Thr Phe Cys Cys Lys Cys Asp
            290                 295                 300

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Cys Pro Ile Cys
                325                 330                 335

Ser Gln Lys Pro Gly Gly Ser Ser Gly Gly Gly Ser Gly Met Phe
            340                 345                 350

Gln Asp Pro Gln Glu Arg Pro Arg Lys Leu Pro Gln Leu Cys Thr Glu
            355                 360                 365

Leu Gln Thr Thr Ile His Asp Ile Ile Leu Glu Cys Val Tyr Cys Lys
            370                 375                 380

Gln Gln Leu Leu Arg Arg Glu Val Tyr Asp Phe Ala Phe Arg Asp Leu
385                 390                 395                 400

Cys Ile Val Tyr Arg Asp Gly Asn Pro Tyr Ala Val Arg Asp Lys Cys
                405                 410                 415

Leu Lys Phe Tyr Ser Lys Ile Ser Glu Tyr Arg His Tyr Cys Tyr Ser
            420                 425                 430

Leu Tyr Gly Thr Thr Leu Glu Gln Gln Tyr Asn Lys Pro Leu Cys Asp
            435                 440                 445

Leu Leu Ile Arg Cys Ile Asn Arg Gln Lys Pro Leu Cys Pro Glu Glu
            450                 455                 460

Lys Gln Arg His Leu Asp Lys Lys Gln Arg Phe His Asn Ile Arg Gly
465                 470                 475                 480

Arg Trp Thr Gly Arg Cys Met Ser Cys Cys Arg Ser Ser Arg Thr Arg
                485                 490                 495

Arg Glu Thr Gln Leu
            500
```

<210> SEQ ID NO 22
<211> LENGTH: 151
<212> TYPE: PRT
<213> ORGANISM: Human papillomavirus

<400> SEQUENCE: 22

Met Phe Gln Asp Pro Gln Glu Arg Pro Arg Lys Leu Pro Gln Leu Cys
1               5                   10                  15

Thr Glu Leu Gln Thr Thr Ile His Asp Ile Ile Leu Glu Cys Val Tyr
            20                  25                  30

Cys Lys Gln Gln Leu Leu Arg Arg Glu Val Tyr Asp Phe Ala Phe Arg
        35                  40                  45

Asp Leu Cys Ile Val Tyr Arg Asp Gly Asn Pro Tyr Ala Val Cys Asp
    50                  55                  60

Lys Cys Leu Lys Phe Tyr Ser Lys Ile Ser Glu Tyr Arg His Tyr Cys
65                  70                  75                  80

Tyr Ser Leu Tyr Gly Thr Thr Leu Glu Gln Gln Tyr Asn Lys Pro Leu
                85                  90                  95

Cys Asp Leu Leu Ile Arg Cys Ile Asn Cys Gln Lys Pro Leu Cys Pro
            100                 105                 110

Glu Glu Lys Gln Arg His Leu Asp Lys Lys Gln Arg Phe His Asn Ile
        115                 120                 125

Arg Gly Arg Trp Thr Gly Arg Cys Met Ser Cys Cys Arg Ser Ser Arg
    130                 135                 140

Thr Arg Arg Glu Thr Gln Leu
145                 150

<210> SEQ ID NO 23
<211> LENGTH: 98
<212> TYPE: PRT
<213> ORGANISM: Human papillomavirus

<400> SEQUENCE: 23

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 24
<211> LENGTH: 158
<212> TYPE: PRT
<213> ORGANISM: Human papillomavirus

<400> SEQUENCE: 24

Met Ala Arg Phe Glu Asp Pro Thr Arg Arg Pro Tyr Lys Leu Pro Asp
1               5                   10                  15

Leu Cys Thr Glu Leu Asn Thr Ser Leu Gln Asp Ile Glu Ile Thr Cys

```
                    20                  25                  30

Val Tyr Cys Lys Thr Val Leu Glu Leu Thr Glu Val Phe Glu Phe Ala
                35                  40                  45

Phe Lys Asp Leu Phe Val Val Tyr Arg Asp Ser Ile Pro His Ala Ala
         50                  55                  60

Cys His Lys Cys Ile Asp Phe Tyr Ser Arg Ile Arg Glu Leu Arg His
 65                  70                  75                  80

Tyr Ser Asp Ser Val Tyr Gly Asp Thr Leu Glu Lys Leu Thr Asn Thr
                 85                  90                  95

Gly Leu Tyr Asn Leu Leu Ile Arg Cys Leu Arg Cys Gln Lys Pro Leu
            100                 105                 110

Asn Pro Ala Glu Lys Leu Arg His Leu Asn Glu Lys Arg Arg Phe His
        115                 120                 125

Asn Ile Ala Gly His Tyr Arg Gly Gln Cys His Ser Cys Cys Asn Arg
    130                 135                 140

Ala Arg Gln Glu Arg Leu Gln Arg Arg Glu Thr Gln Val
145                 150                 155

<210> SEQ ID NO 25
<211> LENGTH: 105
<212> TYPE: PRT
<213> ORGANISM: Human papillomavirus

<400> SEQUENCE: 25

Met His Gly Pro Lys Ala Thr Leu Gln Asp Ile Val Leu His Leu Glu
 1               5                  10                  15

Pro Gln Asn Glu Ile Pro Val Asp Leu Leu Cys His Glu Gln Leu Ser
                20                  25                  30

Asp Ser Glu Glu Glu Asn Asp Glu Ile Asp Gly Val Asn His Gln His
            35                  40                  45

Leu Pro Ala Arg Arg Ala Glu Pro Gln Arg His Thr Met Leu Cys Met
        50                  55                  60

Cys Cys Lys Cys Glu Ala Arg Ile Lys Leu Val Val Glu Ser Ser Ala
 65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 26
<211> LENGTH: 12
<212> TYPE: PRT
<213> ORGANISM: Homo sapiens

<400> SEQUENCE: 26

Glu Leu Lys Thr Pro Leu Gly Asp Thr Thr His Thr
 1               5                  10

<210> SEQ ID NO 27
<211> LENGTH: 15
<212> TYPE: PRT
<213> ORGANISM: Homo sapiens

<400> SEQUENCE: 27

Glu Pro Lys Ser Cys Asp Thr Pro Pro Cys Pro Arg Cys Pro
 1               5                  10                  15

<210> SEQ ID NO 28
```

```
<211> LENGTH: 10
<212> TYPE: PRT
<213> ORGANISM: Artificial
<220> FEATURE:
<223> OTHER INFORMATION: Synthetic

<400> SEQUENCE: 28

Gly Gly Gly Ser Ser Gly Gly Gly Ser Gly
1               5                   10

<210> SEQ ID NO 29
<211> LENGTH: 107
<212> TYPE: PRT
<213> ORGANISM: Homo sapiens

<400> SEQUENCE: 29

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
                20                  25                  30

Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 30
<211> LENGTH: 5
<212> TYPE: PRT
<213> ORGANISM: Artificial
<220> FEATURE:
<223> OTHER INFORMATION: Synthetic

<400> SEQUENCE: 30

Gly Leu Gly Gly Leu
1               5

<210> SEQ ID NO 31
<211> LENGTH: 1506
<212> TYPE: DNA
<213> ORGANISM: Artificial
<220> FEATURE:
<223> OTHER INFORMATION: Synthetic

<400> SEQUENCE: 31
atgcaggtct ccactgctgc ccttgccgtc ctcctctgca ccatggctct ctgcaaccag      60
gtcctctctg caccacttgc tgctgacacg ccgaccgcct gctgcttcag ctacaccctcc    120 cgacagattc cacagaattt catagctgac tactttgaga cgagcagcca gtgctccaag     180
cccagtgtca tcttcctaac caagagaggc cggcaggtct gtgctgaccc cagtgaggag     240
tgggtccaga atacgtcag tgacctggag ctgagtgccg agctcaaaac ccacttggt      300 gacacaactc acacagagcc caaatcttgt gacacacctc cccgtgccc aaggtgccca     360 ggcggtggaa gcagcggagg tggaagtgga ggacagcccc gagaaccaca ggtgtacacc    420 ctgccccat cccggggagga gatgaccaag aaccaggtca gcctgacctg cctggtcaaa    480
```

```
ggcttctacc ccagcgacat cgccgtggag tgggagagca gcgggcagcc ggagaacaac    540
tacaacacca cgcctcccat gctggactcc gacggctcct tcttcctcta cagcaagctc    600
accgtggaca agagcaggtg gcagcagggg aacatcttct catgctccgt gatgcatgag    660
gctctgcaca accgcttcac gcagaagagc ctctccctgt ctccgggtaa aggcctcggt    720
ggcctgatgc atggcgatac cccaacactc catgagtaca tgctggacct tcagcccgag    780
actacggatc tgtatggcta tgggcagttg aatgactcat ctgaggagga ggacgaaata    840
gacggcccag ctggtcaagc cgaaccggat agagcccact acaacattgt gaccttttgc    900
tgtaagtgtg acagcactct gagactgtgt gttcagtcca ctcatgtcga catacgcaca    960
ttggaggatc tcctgatggg aacactggga attgtgtgtc ccatctgttc ccaaaagcct   1020
ggaggtggaa gcagtggagg cggttcaggc atgttccaag atcctcaaga acgtcctcgt   1080
aagctgccac agctgtgtac cgagcttcag accaccattc acgacatcat cctggagtgc   1140
gtctattgca acagcagct ccttagaagg gaagtgtacg attttgcacg gagggacctc   1200
tgcatcgtgt atcgggacgg caatccctat gcggtacggg ataaatgcct gaagttctac   1260
agcaaaatct ccgagtaccg gcactactgc tactctctct atgggacgac tctggaacag   1320
cagtacaaca agcccttgtg cgatctgctg attcgctgca ttaatcgcca gaaacctctg   1380
tgcccagaag agaagcaaag acacctggac aagaaacagc gattccacaa catccgaggg   1440
agatggacag ggaggtgtat gagctgctgt cggagttcta ggacaaggcg cgaaacccag   1500
ctttga                                                               1506
```

<210> SEQ ID NO 32
<211> LENGTH: 501
<212> TYPE: PRT
<213> ORGANISM: Artificial
<220> FEATURE:
<223> OTHER INFORMATION: Synthetic

<400> SEQUENCE: 32

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Ser Gly Gly Gly
        115                 120                 125

Ser Gly Gly Gln Pro Arg Glu Pro Gln Val Tyr Thr Leu Pro Pro Ser
    130                 135                 140

Arg Glu Glu Met Thr Lys Asn Gln Val Ser Leu Thr Cys Leu Val Lys
145                 150                 155                 160

Gly Phe Tyr Pro Ser Asp Ile Ala Val Glu Trp Glu Ser Ser Gly Gln
                165                 170                 175
```

Pro Glu Asn Asn Tyr Asn Thr Thr Pro Pro Met Leu Asp Ser Asp Gly
            180                 185                 190

Ser Phe Phe Leu Tyr Ser Lys Leu Thr Val Asp Lys Ser Arg Trp Gln
        195                 200                 205

Gln Gly Asn Ile Phe Ser Cys Ser Val Met His Glu Ala Leu His Asn
    210                 215                 220

Arg Phe Thr Gln Lys Ser Leu Ser Leu Ser Pro Gly Lys Gly Leu Gly
225                 230                 235                 240

Gly Leu Met His Gly Asp Thr Pro Thr Leu His Glu Tyr Met Leu Asp
            245                 250                 255

Leu Gln Pro Glu Thr Thr Asp Leu Tyr Gly Tyr Gly Gln Leu Asn Asp
        260                 265                 270

Ser Ser Glu Glu Glu Asp Glu Ile Asp Gly Pro Ala Gly Gln Ala Glu
    275                 280                 285

Pro Asp Arg Ala His Tyr Asn Ile Val Thr Phe Cys Cys Lys Cys Asp
290                 295                 300

Ser Thr Leu Arg Leu Cys Val Gln Ser Thr His Val Asp Ile Arg Thr
305                 310                 315                 320

Leu Glu Asp Leu Leu Met Gly Thr Leu Gly Ile Val Cys Pro Ile Cys
            325                 330                 335

Ser Gln Lys Pro Gly Gly Gly Ser Ser Gly Gly Gly Ser Gly Met Phe
        340                 345                 350

Gln Asp Pro Gln Glu Arg Pro Arg Lys Leu Pro Gln Leu Cys Thr Glu
    355                 360                 365

Leu Gln Thr Thr Ile His Asp Ile Ile Leu Glu Cys Val Tyr Cys Lys
370                 375                 380

Gln Gln Leu Leu Arg Arg Glu Val Tyr Asp Phe Ala Arg Arg Asp Leu
385                 390                 395                 400

Cys Ile Val Tyr Arg Asp Gly Asn Pro Tyr Ala Val Arg Asp Lys Cys
            405                 410                 415

Leu Lys Phe Tyr Ser Lys Ile Ser Glu Tyr Arg His Tyr Cys Tyr Ser
        420                 425                 430

Leu Tyr Gly Thr Thr Leu Glu Gln Gln Tyr Asn Lys Pro Leu Cys Asp
    435                 440                 445

Leu Leu Ile Arg Cys Ile Asn Arg Gln Lys Pro Leu Cys Pro Glu Glu
450                 455                 460

Lys Gln Arg His Leu Asp Lys Lys Gln Arg Phe His Asn Ile Arg Gly
465                 470                 475                 480

Arg Trp Thr Gly Arg Cys Met Ser Cys Cys Arg Ser Ser Arg Thr Arg
            485                 490                 495

Arg Glu Thr Gln Leu
            500

<210> SEQ ID NO 33
<211> LENGTH: 1506
<212> TYPE: DNA
<213> ORGANISM: Artificial
<220> FEATURE:
<223> OTHER INFORMATION: Synthetic

<400> SEQUENCE: 33
atgcaggtct ccactgctgc ccttgccgtc ctcctctgca ccatggctct ctgcaaccag    60
gtcctctctg caccacttgc tgctgacacg ccgaccgcct gctgcttcag ctacaccctcc   120 cgacagattc cacagaattt catagctgac tactttgaga cgagcagcca gtgctccaag   180

```
cccagtgtca tcttcctaac caagagaggc cggcaggtct gtgctgaccc cagtgaggag      240
tgggtccaga atacgtcag tgacctggag ctgagtgccg agctcaaaac cccacttggt       300
gacacaactc acacagagcc caaatcttgt gacacacctc ccccgtgccc aaggtgccca      360
ggcggtggaa gcagcggagg tggaagtgga ggacagcccc gagaaccaca ggtgtacacc      420
ctgcccccat cccgggagga gatgaccaag aaccaggtca gcctgacctg cctggtcaaa      480
ggcttctacc ccagcgacat cgccgtggag tgggagagca gcgggcagcc ggagaacaac      540
tacaacacca cgcctcccat gctggactcc gacggctcct tcttcctcta cagcaagctc      600
accgtggaca gagcaggtg gcagcagggg aacatcttct catgctccgt gatgcatgag       660
gctctgcaca accgcttcac gcagaagagc ctctccctgt ctccgggtaa aggcctcggt      720
ggcctgatgc atggtgacac accaaccctg cacgaataca tgctcgatct gcagccagag      780
actaccgacc tttacggcta tgggcagttg aacgacagct ctgaggagga ggacgagatc      840
gatggtcctg ctggacaagc agaaccagac agagcccact acaacatcgt aaccttttgc      900
tgcaagtgtg acagtaccct tcgtttgtgc gttcagagca cgcatgtcga cattcggaca      960
ctggaggatc tgctcatggg gactctgggg attgtgtgtc ctatttgcag ccagaaacca     1020
ggcggaggat cttcaggagg cgggagtggc atgttccaag accctcagga cgccctcgg     1080 aaactgcccc aattgtgtac tgagctccag acaacgatac acgacataat cctggagtgc    1140
gtgtattgca agcagcagct tctgaggagg gaagtgtacg attttgccag agagatggc     1200 tgcattgtct accgagatgg caatccctat gcggtgtgtg ataagtgtct gaagttctat    1260
tccaaaatca gcgaatatcg gcattattgc tactcactgt acggaactac cctcgaacag    1320
cagtacaaca aaccgctctg tgatctgctg atcagatgca tcaatcggca gaaaccctt     1380 tgtcccgaag agaagcaaag acacctggac aagaagcaga ggttccacaa tacccgaggt    1440
cgttggactg ggcgctgcat gtcctgttgt cgctcctctc gcacaaggag agagacacaa    1500
ctgtga                                                                1506
```

<210> SEQ ID NO 34
<211> LENGTH: 501
<212> TYPE: PRT
<213> ORGANISM: Artificial
<220> FEATURE:
<223> OTHER INFORMATION: Synthetic

<400> SEQUENCE: 34

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
            20                  25                  30

Ala Cys Cys Phe Ser Tyr Thr Ser Arg Gln Ile Pro Gln Asn Phe Ile
        35                  40                  45

Ala Asp Tyr Phe Glu Thr Ser Ser Gln Cys Ser Lys Pro Ser Val Ile
    50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala Glu Leu Lys
                85                  90                  95

Thr Pro Leu Gly Asp Thr Thr His Thr Glu Pro Lys Ser Cys Asp Thr
            100                 105                 110

Pro Pro Pro Cys Pro Arg Cys Pro Gly Gly Gly Ser Ser Gly Gly Gly
        115                 120                 125
```

```
Ser Gly Gly Gln Pro Arg Glu Pro Gln Val Tyr Thr Leu Pro Pro Ser
    130                 135                 140
Arg Glu Glu Met Thr Lys Asn Gln Val Ser Leu Thr Cys Leu Val Lys
145                 150                 155                 160
Gly Phe Tyr Pro Ser Asp Ile Ala Val Glu Trp Glu Ser Ser Gly Gln
            165                 170                 175
Pro Glu Asn Asn Tyr Asn Thr Thr Pro Pro Met Leu Asp Ser Asp Gly
                180                 185                 190
Ser Phe Phe Leu Tyr Ser Lys Leu Thr Val Asp Lys Ser Arg Trp Gln
        195                 200                 205
Gln Gly Asn Ile Phe Ser Cys Ser Val Met His Glu Ala Leu His Asn
    210                 215                 220
Arg Phe Thr Gln Lys Ser Leu Ser Leu Ser Pro Gly Lys Gly Leu Gly
225                 230                 235                 240
Gly Leu Met His Gly Asp Thr Pro Thr Leu His Glu Tyr Met Leu Asp
            245                 250                 255
Leu Gln Pro Glu Thr Thr Asp Leu Tyr Gly Tyr Gly Gln Leu Asn Asp
                260                 265                 270
Ser Ser Glu Glu Glu Asp Glu Ile Asp Gly Pro Ala Gly Gln Ala Glu
        275                 280                 285
Pro Asp Arg Ala His Tyr Asn Ile Val Thr Phe Cys Cys Lys Cys Asp
290                 295                 300
Ser Thr Leu Arg Leu Cys Val Gln Ser Thr His Val Asp Ile Arg Thr
305                 310                 315                 320
Leu Glu Asp Leu Leu Met Gly Thr Leu Gly Ile Val Cys Pro Ile Cys
            325                 330                 335
Ser Gln Lys Pro Gly Gly Gly Ser Ser Gly Gly Gly Ser Gly Met Phe
            340                 345                 350
Gln Asp Pro Gln Glu Arg Pro Arg Lys Leu Pro Gln Leu Cys Thr Glu
            355                 360                 365
Leu Gln Thr Thr Ile His Asp Ile Ile Leu Glu Cys Val Tyr Cys Lys
    370                 375                 380
Gln Gln Leu Leu Arg Arg Glu Val Tyr Asp Phe Ala Arg Arg Asp Gly
385                 390                 395                 400
Cys Ile Val Tyr Arg Asp Gly Asn Pro Tyr Ala Val Cys Asp Lys Cys
            405                 410                 415
Leu Lys Phe Tyr Ser Lys Ile Ser Glu Tyr Arg His Tyr Cys Tyr Ser
            420                 425                 430
Leu Tyr Gly Thr Thr Leu Glu Gln Gln Tyr Asn Lys Pro Leu Cys Asp
            435                 440                 445
Leu Leu Ile Arg Cys Ile Asn Arg Gln Lys Pro Leu Cys Pro Glu Glu
    450                 455                 460
Lys Gln Arg His Leu Asp Lys Lys Gln Arg Phe His Asn Thr Arg Gly
465                 470                 475                 480
Arg Trp Thr Gly Arg Cys Met Ser Cys Cys Arg Ser Ser Arg Thr Arg
            485                 490                 495
Arg Glu Thr Gln Leu
            500
```

VACCINES AGAINST HPV

CROSS-REFERENCE TO RELATED APPLICATIONS

This application is the U.S. National Stage of International Application PCT/EP2012/076404 filed Dec. 20, 2012, which designates the U.S. and was published by the International Bureau in English on Jun. 27, 2013, and which claims the benefit of U.S. Provisional Application No. 61/578,542, filed Dec. 21, 2011, both of which are hereby incorporated by reference in their entirety.

FIELD OF THE INVENTION

The present invention relates to therapeutic compounds, such as vaccines against human papillomavirus (HPV) and in particular to DNA vaccines against HPV16 and/or HPV18. The invention further relates to protein construct encoding homodimeric peptides, which peptides may be released from a DNA vaccine or used separately. Further described are pharmaceutical formulations, host cells and methods for producing the vaccines, as well as methods for the treatment of various HPV induced diseases, such as cancers and infectious diseases by application.

BACKGROUND OF THE INVENTION

It is now well established that human papillomavirus (HPV) is the cause of cervical cancer and other HPV-associated malignancies such as anogenital (anus, vulvar, vaginal and penile) cancers and a subset of head and neck cancers. In particular, HPV16 and HPV 18 are responsible for about 70% of all cervical cancers worldwide.

To date, two prophylactic HPV vaccines are on the market (Gardasil and Cervarix). The aim of the prophylactic vaccines is to induce humoral immune responses by stimulating the production of neutralizing antibodies specific for the HPV viral capsid proteins, L1 and L2. Although the preventive vaccines are an important milestone for the control of HPV induced cervical cancer and possibly other HPV-associated malignancies, the effect of these vaccines will not be significantly observed for 20-40 years (Ma B et al., Current Cancer Therapy Reviews, 2010). Moreover, since the coverage of mass vaccination for the prophylactic vaccines are to date limited in addition to a substantial population worldwide that already are HPV infected, HPV-associated malignancies will continue to progress. Thus, it will be important to develop HPV-specific therapeutic vaccines in order to reduce the mortality and morbidity of HPV-associated malignancies and its precursor lesions (Ma B et al., Current Cancer Therapy Reviews, 2010).

The development of various cancer vaccines and cancer immunotherapy strategies has throughout the last two decades expanded. Still, only one therapeutic cancer vaccine, called Provenge (Dendreon INC) has so far been approved to be applied as standard therapy for prostate cancer. Notably, due to ethical reasons the majority of therapeutic cancer vaccines are tested on a patient group bearing a late stage tumor. This patient group is substantially immunosuppressed meaning that the tumor cells have for long escaped the immune system and contributed to induce immunological tolerance to the tumor along carcinogenesis. In addition, the choice of antigens (tumor-specific vs. tumor-associated) applied as vaccines are critical in order to induce tumor-specific immune responses and avoid killing of healthy cells in the patients which may lead to serious adverse events. Thus, the major challenges in cancer immunotherapy are to break the immunological tolerance and activate tumor-specific effector functions to recognize and kill tumor cells. Although some case reports show clinical response to therapeutic cancer vaccines in late stage tumor patients, the most common primary endpoint is to observe the impact on overall survival compared to conventional therapy (surgery, chemo and radiation therapy). However, most studies are either not conclusive or that they completely fail to show this. One reason for the negative results lies in the patient group carrying end-stage tumors that are challenging to treat in the first place. A possible strategy could be to include patients with early-stage tumors in therapeutic vaccine trials.

One strategy is to target pre-cancerous lesions. The challenges for this strategy are mainly the lack of reliable biomarkers that are specifically expressed by precancerous lesions for many tissues and poor medical screening (either non-existing or that the existing method suffers from lack of sensitivity). Exceptionally, this is not the case for HPV-induced malignancies. For instance, the majority of western countries have good screening programs for cervical dysplasia and cervical cancer by performing the papanicolaou test (Pap smear test). If there are unclear or abnormal results from Pap smear test, colposcopy will be performed (National Cervical Cancer Coalition). HPV-testing may also be recommended for some patients to detect the presence of "high-risk" HPV-type in the precancerous lesion. Thus, HPV represents a potential biomarker for HPV-associated precancerous lesions, in particular cervical intraepithelial dysplasia (CIN).

DNA vaccines have shown increasing promise for the treatment of human diseases, in particular cancer. DNA vaccines induce strong antigen-specific immune responses and can be repeatedly administered to maintain the target-specific immune responses. Such vaccines are considered to be safe and simple and cheap to produce on a large scale compared to other cancer therapeutic formats. Numerous immunotherapeutic interventions fail to induce immunological memory. Exceptionally, DNA vaccination ensures sustained release of the vaccine product in vivo which enhances antigen-specific immunological memory. Direct delivery of antigens to professional antigen-presenting cells (APCs) stimulates both CD4+ and CD8+ T cell immune responses in vivo. Such strong cellular immune responses have been demonstrated to specifically recognize and kill antigen-positive malignant cells efficiently both in vitro and in vivo.

There is still a need in the art for improved vaccines for inducing strong and specific immune responses against HPV responsible for both infectious diseases and cancers.

OBJECT OF THE INVENTION

It is an object of embodiments of the invention to provide specific and highly effective therapeutic compounds, such as DNA vaccines against diseases and conditions caused by HPV.

SUMMARY OF THE INVENTION

It has been found by the present inventors that by combining the antigens of the early gene products E6 and E7 from HPV, such as from HPV16 and/or HPV18 with the targeting module of hMIP-1α, therapeutic vaccines are provided, wherein the strong immunogenic epitopes of HPV gene products are presented with high efficiency to APCs to induce a specific and strong immune response. The products according to the present invention is primarily envisioned as therapeutic nucleic acid vaccines, such as DNA vaccines, wherein a nucleic acid construct encoding the vaccibody construct is used as the therapeutic compound leading to in vivo production of the protein product within the person receiving the vaccine. However, as an alternative the protein product itself may be formulated and used directly in the vaccine.

Accordingly, in a first aspect the present invention relates to a homodimeric protein of two identical amino acid chains, each amino acid chain comprising (1) a signal peptide, (2) a targeting unit, (3) a dimerization motif, and (4) an antigenic unit, said targeting unit comprising an amino acid sequence having at least 80% sequence identity to the amino acid sequence 24-93 of SEQ ID NO:1, and an antigenic unit comprising an amino acid sequence of human papillomavirus (HPV), such as an antigenic unit comprising an amino acid sequence of HPV16 and/or HPV18, such as an antigenic unit derived from early proteins E6 and/or E7 of HPV16 and/or HPV18.

In a second aspect the present invention relates to an amino acid chain comprising (1) a signal peptide, (2) a targeting unit, (3) a dimerization motif, and (4) an antigenic unit, said targeting unit comprising an amino acid sequence having at least 80% sequence identity to the amino acid sequence 24-93 of SEQ ID NO:1, and an antigenic unit comprising an amino acid sequence of human papillomavirus (HPV), such as an antigenic unit comprising an amino acid sequence of HPV16 and/or HPV18, such as an antigenic unit derived from early proteins E6 and/or E7 of HPV16 and/or HPV18, which amino acid chain is able to form a homodimeric protein according to the invention.

In a third aspect the present invention relates to a nucleic acid molecule, such as a DNA, encoding an amino acid chain comprising (1) a signal peptide, (2) a targeting unit, (3) a dimerization motif, and (4) an antigenic unit, said targeting unit comprising an amino acid sequence having at least 80% sequence identity to the amino acid sequence 24-93 of SEQ ID NO:1, and an antigenic unit comprising an amino acid sequence of human papillomavirus (HPV), such as an antigenic unit comprising an amino acid sequence of HPV16 and/or HPV18, such as an antigenic unit derived from early proteins E6 and/or E7 of HPV16 and/or HPV18, which amino acid chain is able to form a homodimeric protein according to the invention.

In a further aspect the present invention relates to a homodimeric protein according to the invention, or an amino acid chain according to the invention, or the nucleic acid molecule according to the invention for use as a medicament.

In a further aspect the present invention relates to a pharmaceutical composition comprising a homodimeric protein according to the invention, or an amino acid chain according to the invention, or the nucleic acid molecule according to the invention.

In a further aspect the present invention relates to a host cell comprising the nucleic acid molecule according to the invention.

In a further aspect the present invention relates to a method for preparing a homodimeric protein according to the invention, or an amino acid chain of the invention, the method comprising a) transfecting the nucleic acid molecule according to the invention into a cell population; b) culturing the cell population; c) collecting and purifying the homodimeric protein, or amino acid chain expressed from the cell population.

In a further aspect the present invention relates to a method for preparing a vaccine, such as a DNA vaccine, comprising an immunologically effective amount of a nucleic acid molecule according to the invention, the method comprising a) preparing a nucleic acid molecule according to the invention; b) dissolving the nucleic acid molecule obtained under step a) in a pharmaceutically acceptable carrier, diluent, or buffer.

In a further aspect the present invention relates to a vaccine against HPV comprising an immunologically effective amount of a homodimeric protein according to the invention, or an amino acid chain according to the invention, or nucleic acid molecule, such as a DNA, according to the invention, wherein said vaccine is able to trigger both a T-cell- and B-cell immune response.

In a further aspect the present invention relates to a method of treating or preventing a HPV induced disease or condition, such as a cancer or an infectious disease caused by HPV in a patient, the method comprising administering to the patient in need thereof, a homodimeric protein according to the invention, or an amino acid chain according to the invention, or the nucleic acid molecule, such as a DNA, according to the invention.

LEGENDS TO THE FIGURE

FIG. 1: The overall structure of vaccibody vaccines with E7/E6 fusion antigen. Shown are both DNA and protein formats. The vaccibody consist of three functional modules; the chemokine human MIP-1α (LD78β) in the targeting module, hinge and CH3 sequences from human IgG3 in the dimerization module and full-length E7 and/or E6 fusion in the vaccine module.

Figure 2:
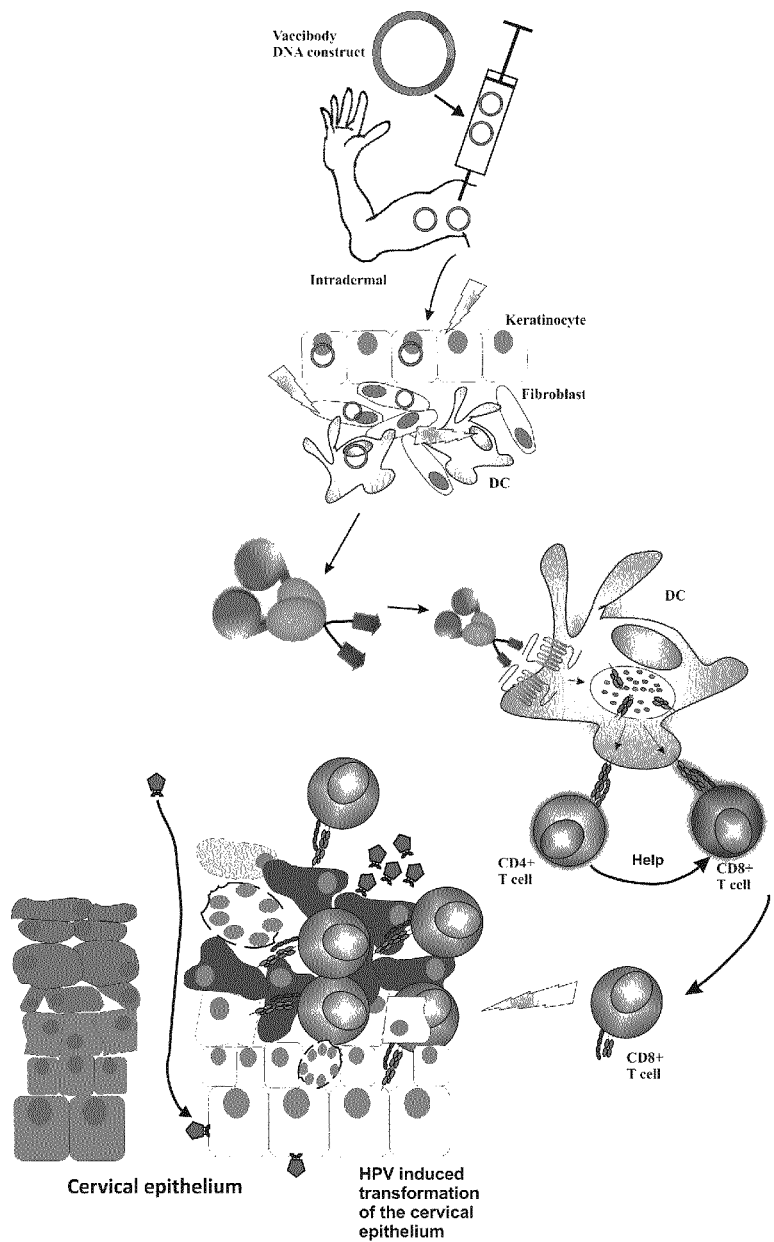

FIG. 2: The suggested mode of action for a Vaccibody DNA vaccine against HPV-induced malignancies. Naked DNA plasmid encoding vaccibody is injected intradermal followed by electroporation. The plasmid is taken up by local cells and vaccibody proteins are produced and secreted. The chemotactic targeting modules attract CCR1 and CCR5 expressing antigen presenting cells (APC) and ensure binding and uptake into dendritic cells (DC). The DC will present antigenic peptides to CD4+ and CD8+ T cells and the CD8+ T cells will kill HPV infected and transformed cells in the cervix.

Figure 3:
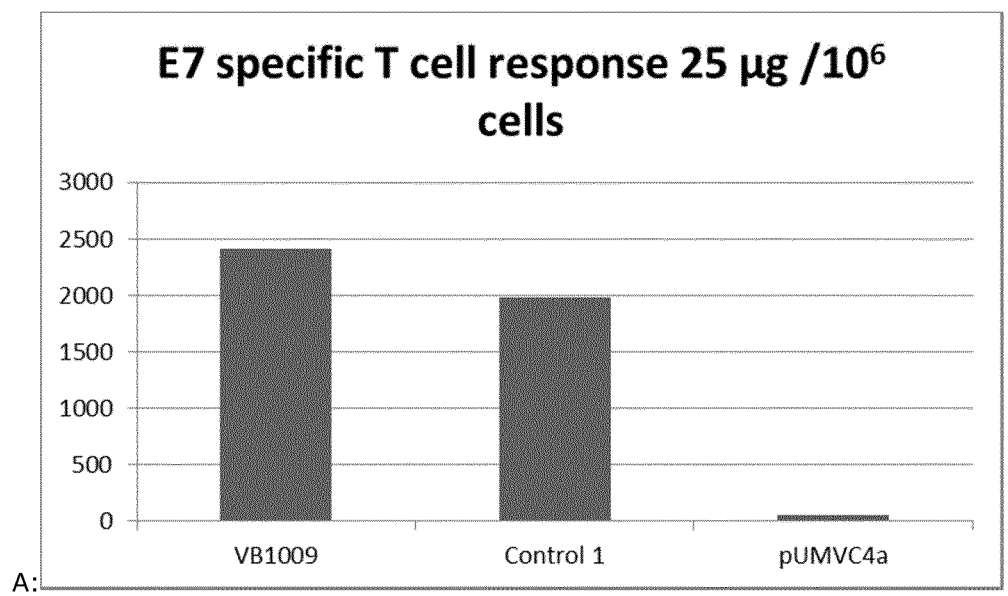
Figure 3:
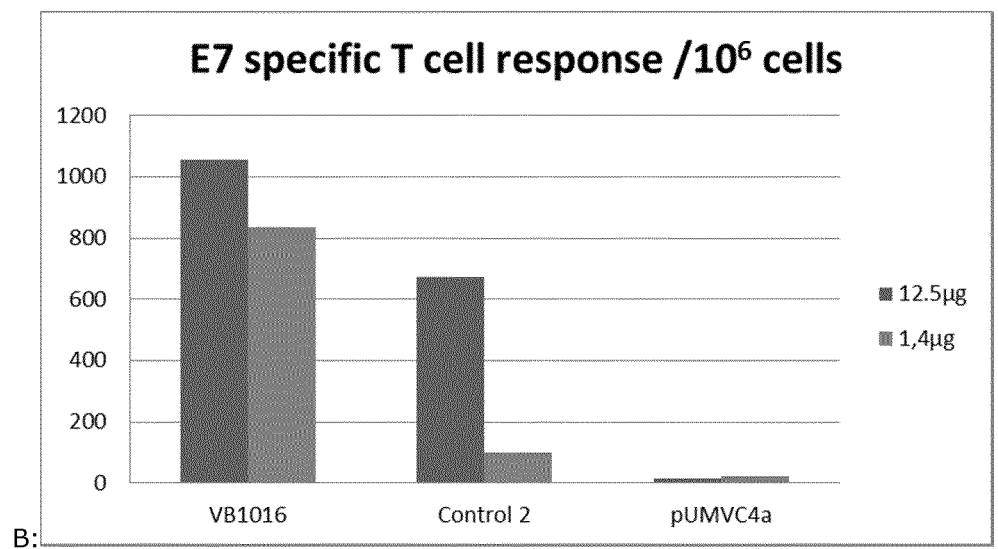

FIG. 3: ELISPOT results showing the number of E7 and E6 specific T cell responses as a function of different amounts of vaccine administered. C57BL/6 mice were injected i.d. with naked DNA plasmids encoding VB1009 and VB1016 and their corresponding controls followed by electroporation (Cellectis, France) on day 0 and day 7. Splenocytes were harvested at day 21 and stimulated with MHC class I-restricted E7 or E6 peptide for 24 h. The number of IFNγ secreting splenocytes was calculated by ELISPOT. (A) E7-specific responses after i.d. vaccination with 25 µg of VB1009, control 1 (antigen alone) and pUMVC4a (empty vector). (B) E7-specific responses after i.d. vaccination with 12.5 and 1.4 µg of VB1016, control 2 (antigen alone) and pUMVC4a (empty vector). (C) E6-specific responses after i.d. vaccination with 12.5 and 1.4 µg of VB1016, control 2 (antigen alone) and pUMVC4a (empty vector).

FIG. 4. Therapeutic effect of VB1016 shown by measured tumor volume. C57BL/6 mice were injected s.c. with $5 \times 10^5$ TC-1 cells at day 0. At day 3 and day 10, the mice were injected i.d. with 12.5 µg naked DNA plasmids encoding VB1016, control 2 or empty vector followed by electroporation (Cellectis, France). The tumor sizes were measured by caliper two to three times a week and tumor volume calculated.

Figure 5:
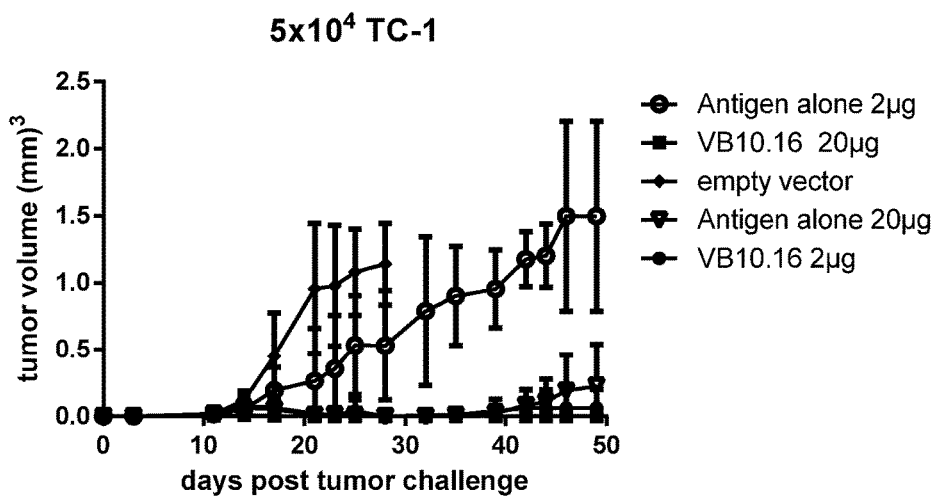

FIG. 5. Therapeutic effect of VB1016 shown by measured tumor volume. C57BL/6 mice were injected s.c. in the neck area with $5\times10^4$ TC-1 cells at day 0. At day 3,7 and day 10, the mice were injected i.d. with 20 µg or 2 µg naked DNA plasmids encoding VB1016, control 2 or empty vector followed by electroporation (Cellectis, France). The tumor sizes were measured by caliper two to three times a week and tumor volume calculated.

Figure 6:
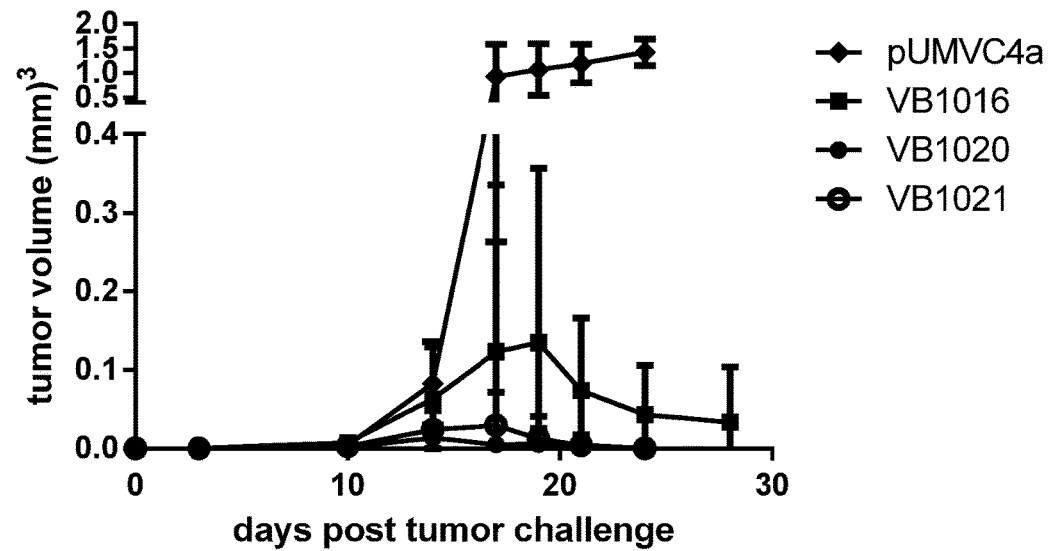

FIG. 6. Therapeutic effect of VB1020 and VB1021 shown by measured tumor volume. C57BL/6 mice were injected s.c. in the thigh with $5\times10^4$ TC-1 cells at day 0. At day 3 and day 10, the mice were injected i.d. with 10 µg naked DNA plasmids encoding VB1016, VB1020, VB1021 or empty vector followed by electroporation (Cellectis, France). The tumor sizes were measured by caliper two to three times a week and tumor volume calculated.

DETAILED DISCLOSURE OF THE INVENTION

The constructs and DNA vaccine technology described herein by the inventors of the present invention (also referred to as "vaccibody" molecules/vaccines/constructs) represents a novel vaccine strategy to induce strong and specific immune responses for both infectious diseases and cancer. The HPV E6/E7, such as HPV16 or HPV18 E6/E7 vaccine described herein may be administered as a DNA vaccine by intradermal injection, preferably followed by electroporation. This results in the uptake of the DNA-construct encoding the vaccibody-HPV16 and/or HPV18 E6/E7 vaccine in cells at the site of injection (dermis) including dendritic cells (Langerhans cells), leading to in vivo production of the vaccibody-E6/E7 molecule.

The early gene products E6 and E7 from "high-risk" HPV types such as HPV16 and 18 may be responsible for transformation of the basal-epithelium cells and induction of precancerous lesions. Both proteins consist of highly immunogenic epitopes and are shown herein to induce strong immune responses leading to specific eradication of "high-risk" HPV positive tumor cells both in vitro and in vivo.

The vaccibody molecule described herein is a homodimer consisting of three modules; targeting module, dimerization module and the vaccine module (FIG. 1). Genes encoding the three modules are genetically engineered to be expressed as one gene. When expressed in vivo, the vaccibody molecule targets antigen presenting cells (APCs) which results in an enhanced vaccine potency compared to identical, non-targeted antigens. In vivo expression of the chemokine human macrophage inflammatory protein 1 alpha (hMIP-1α/LD78β) leads to attraction of DCs, neutrophils and other immune cells carrying the CCR1 and CCR5 receptors to the site of expression. Thus, the vaccibody molecule consisting of hMIP-1α as the targeting module, will not only target the antigens to specific cells, but in addition give a response-amplifying effect (adjuvant effect) by recruiting specific immune cells to the injection site. This unique mechanism may be of great importance in a clinical setting where patients can receive the vaccine without any additional adjuvants since the vaccine itself gives the adjuvant effect.

The inventors of the present invention describes herein vaccine constructs where the antigenic module consist of the E7 full length genetic sequence in fusion to the E6 full length sequence originating from the HPV16 or HPV18 subtype. The advantage of this format is that both E6 and E7 will be present in one construct and may thus be equally expressed in vivo. Consequently, one vaccibody molecule consisting of a multi-antigenic unit may represent equal levels of E6 and E7 for the immune system. The HPV16 E6 and E7 gene products are oncogenic in their natural form. To neutralize their oncogenic properties, mutations at specific sites may be introduced in the E6 and E7 genetic sequence.

The mutations, including deletions, may be introduced at specific sites, known to inhibit the oncogenic properties of E6 and E7, such as any one described in any of Dalal S et al., *J Virol*, 1996; Münger K et al., *EMBO*, 1989; Nakagawa S et al., *Virology*, 1995; Crook T et al., *Cell*, 1991; Münger K et al., *HPV Compendium Online*, 1997 (http://www.stdgen.lanl.gov/COMPENDIUM_PDF/97PDF/3/E7.pdf); Nguyen, M et al., *J Virol*, 2002; Nominé Y et a., *Molecular Cell*, 2006; Moody C et al., *Nat Rev Cancer*, 2010, Polakova I et al., *Vaccine*, 2010; Xie Q, *Virologica Sinica*, 2011; Mesplède T et al., *J Virol*, 2012; US 2008/0102084 and U.S. Pat. No. 6,306,397, which references are hereby incorporated by reference. Accordingly, in some aspects of the invention, the constructs according to the present invention contain HPV16 E6, E7 or HPV16 E6/E7 chimeric constructs with one or more mutations in either of HPV16 E6, E7 or both at a position known to inhibit the oncogenic properties as described in Dalal S et al., 3 Virol, 1996; Münger K et al., EMBO, 1989; Nakagawa S et al., Virology, 1995; Crook T et al., Cell, 1991; Münger K et al., HPV Compendium Online, 1997 (http://www.stdgen.lanl.gov/COMPENDIUM_PDF/97PDF/3/E7.pdf); Nguyen, M et al., *J Virol*, 2002; Nominé Y et a., *Molecular Cell*, 2006; Moody C et al., Nat Rev Cancer, 2010, Polakova I et al., *Vaccine*, 2010; Xie Q, *Virologica Sinica*, 2011; Mesplède T et al., *J Virol*, 2012; US 2008/0102084 or U.S. Pat. No. 6,306,397. In other aspects of the invention, the constructs according to the present invention contain HPV18 E6, E7 or HPV18 E6/E7 chimeric constructs with one or more mutations in either of HPV18 E6, E7 or both at a position known to inhibit the oncogenic properties as described in Dalal S et al., J Virol, 1996; Münger K et al., EMBO, 1989; Nakagawa S et al., Virology, 1995; Crook T et al., Cell, 1991; Münger K et al., HPV Compendium Online, 1997 (http://www.stdgen.lanl.gov/COMPENDIUM_PDF/97PDF/3/E7.pdf); Moody C et al., Nat Rev Cancer, 2010, US 2008/0102084 and U.S. Pat. No. 6,306,397.

There is a possibility that the vaccibody-moiety (targeting and dimerization modules) may eradicate the oncogenic properties of E6 and E7 wildtype proteins in the final fusion protein. Thus, in yet another aspect of the invention is the utilization of the wildtype full-length E6 and/or E7 sequences in the vaccibody construction.

The invention describes several variant of Vaccibody HPV therapeutic DNA vaccines all based on the overall format described in FIG. 1, the therapeutic vaccibody-HPV DNA vaccines encodes genes that are naturally expressed in humans; the targeting module genes encode the chemokine hMIP-1α, which binds to its cognate receptors, CCR1 and CCR5 expressed on the cell surface of APCs. The dimerization module genes may encode hinge regions and constant heavy chain 3, such as from human IgG3 which connects two vaccibody monomers generating a homodimer molecule. Genes encoding the vaccine module for the current strategy consist of HPV, such as HPV16 and/or HPV18 E7 and E6 antigens, such as the full length HPV16 E7 and E6 antigens, optionally comprising one or more mutation to inhibit the oncogenic properties. Once administered in vivo by i.d. injection followed by electroporation, dermal cells taking up the vaccine construct will express the vaccibody-HPV molecule. The in vivo produced vaccibody vaccines target to CCR1 and CCR5 expressed on the surface of APCs in the skin, in particular DCs. The binding of the vaccibody molecule to its cognate receptors leads to internalization of the complex in the APC, degradation of the proteins into small peptides that are loaded onto MHC molecules and presented to CD4$^+$ and CD8$^+$ T cells to induce HPV16 E6 and E7 specific immune responses. Once stimulated and with help from activated CD4$^+$ T cells, CD8$^+$ T cells will target and kill HPV16 E6 and E7 expressing cells (FIG. 2). Such enhanced immune responses to a vaccine with a "built-in" adjuvant effect may potentially overcome tumor-escape (tumor immune surveillance) by breaking immunological tolerance and efficiently kill malignant cells. The hMIP-1α targeting unit may be connected through a dimerization motif, such as a hinge region, to an antigenic unit, wherein the later is in either the COOH-terminal or the NH2-terminal end. The present invention not only relates to a DNA sequence coding for this recombinant protein, but also to expression vectors comprising these DNA sequences, cell lines comprising said expression vectors, to treatment of mammals preferentially by immunization by means of Vaccibody DNA, Vaccibody RNA, or Vaccibody protein, and finally to pharmaceuticals and a kit comprising the said molecules.

The dimerization motif in the proteins according to the present invention may be constructed to include a hinge region and an immunoglobulin domain (e.g. Cγ3 domain), e.g. carboxyterminal C domain ($C_H3$ domain), or a sequence that is substantially identical to said C domain. The hinge region may be Ig derived and contributes to the dimerization through the formation of an interchain covalent bond(s), e.g. disulfide bridge(s). In addition, it functions as a flexible spacer between the domains allowing the two targeting units to bind simultaneously to two target molecules on APC expressed with variable distances. The immunoglobulin domains contribute to homodimerization through non-covalent interactions, e.g. hydrophobic interactions. In a preferred embodiment the $C_H3$ domain is derived from IgG. These dimerization motifs may be exchanged with other multimerization moieties (e.g. from other Ig isotypes/subclasses). Preferably the dimerization motif is derived from native human proteins, such as human IgG.

It is to be understood that the dimerization motif may have any orientation with respect to antigenic unit and targeting unit. In one embodiment the antigenic unit is in the COOH-terminal end of the dimerization motif with the targeting unit in the N-terminal end of the dimerization motif. In another embodiment the antigenic unit is in the N-terminal end of the dimerization motif with the targeting unit in the COOH-terminal end of the dimerization motif.

International application WO 2004/076489, which is hereby incorporated by reference discloses nucleic acid sequences and vectors, which may be used according to the present invention.

The proteins according to the present invention include an antigenic unit derived from HPV, such as HPV16 E7 and E6 antigens, such as the full length HPV16 E7 and E6 antigens, as well as immunogenic fragments or variants thereof. The antigenic sequence should be of sufficient length. The minimal length of such antigenic unit may be around 9 amino acids. Accordingly in some embodiments, the antigenic unit derived from HPV comprises an amino acid sequence of at least 9 amino acids corresponding to at least about 27 nucleotides in a nucleic acids sequence encoding such antigenic unit. Preferably the antigenic unit derived from HPV is considerably longer, such as the full length HPV16 E7 and E6 antigens. Diversity arises within a given HPV genotype through limited nucleotide changes in the coding (at a frequency of <2%) and non-coding (at a frequency of <5%) regions (Bernard, H U et al., Int J Cancer, 2006). Such variants phylogenetically segregate based on their geographical origin and are therefore labeled European, African, Asian, Asian-American and North American. Insertion of such sequences in a Vaccibody format might lead to activation of both arms of the immune response.

Immunization by means of Vaccibody protein, Vaccibody DNA, or Vaccibody RNA, the latter two executed e.g. by intramuscular or intradermal injection with or without a following electroporation, are all feasible methods according to the present invention.

As discussed above, the present invention relates to a vaccine composition against cancer or infectious diseases caused by HPV, the vaccine composition comprising an immunologically effective amount of the nucleic acid encoding the molecule of the invention or degenerate variants thereof. The vaccine may be able to trigger both a T-cell- and B-cell immune response. The present invention also relates to a kit comprising Vaccibody DNA, RNA, or protein for diagnostic, medical or scientific purposes.

The invention further relates to a method of preparing the recombinant molecule of the invention comprising, transfecting the vector comprising the molecule of the invention into a cell population; culturing the cell population; collecting recombinant protein expressed from the cell population; and purifying the expressed protein.

The above described nucleotide sequences may be inserted into a vector suited for gene therapy, e.g. under the control of a specific promoter, and introduced into the cells. In some embodiments the vector comprising said DNA sequence is a virus, e.g. an adenovirus, vaccinia virus or an adeno-associated virus. In some embodiments a retroviruses is used as vector. Examples of suitable retroviruses are e.g. MoMuLV or HaMuSV. For the purpose of gene therapy, the DNA/RNA sequences according to the invention can also be transported to the target cells in the form of colloidal dispersions. They comprise e.g. liposomes or lipoplexes.

The present invention encompasses the use of a targeting unit as well as an antigenic unit having minimum degree of sequence identity or sequence homology with amino acid sequence(s) defined herein or with a polypeptide having the specific properties defined herein. The present invention encompasses, in particular, the use of peptide variants or peptide units to be used in the constructs according to the present invention having a degree of sequence identity with any one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34. Here, the term "variant" means an entity having a certain degree of sequence identity with the subject amino acid sequences or the subject nucleotide sequences, where the subject amino acid sequence preferably is SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, or SEQ ID NO:34.

In one aspect, the variant or fragment amino acid sequence and/or nucleotide sequence should provide and/or encode a polypeptide which retains the functional activity and/or enhances the activity of a polypeptide of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34.

In the present context, a variant sequence is taken to include an amino acid sequence which may be at least 80%, at least 85%, at least 90%, at least 95%, at least 96%, at least 97%, at least 98% or at least 99%, identical to the subject sequence. Typically, the variants used according to the present invention will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

Sequence identity comparisons can be conducted by eye, or more usually, with the aid of readily available sequence comparison computer programs. These commercially available computer programs use complex comparison algorithms to align two or more sequences that best reflect the evolutionary events that might have led to the difference(s) between the two or more sequences. Therefore, these algorithms operate with a scoring system rewarding alignment of identical or similar amino acids and penalising the insertion of gaps, gap extensions and alignment of non-similar amino acids. The scoring system of the comparison algorithms include:

i) assignment of a penalty score each time a gap is inserted (gap penalty score),
ii) assignment of a penalty score each time an existing gap is extended with an extra position (extension penalty score),
iii) assignment of high scores upon alignment of identical amino acids, and
iv) assignment of variable scores upon alignment of non-identical amino acids.

Most alignment programs allow the gap penalties to be modified. However, it is preferred to use the default values when using such software for sequence comparisons.

The scores given for alignment of non-identical amino acids are assigned according to a scoring matrix also called a substitution matrix. The scores provided in such substitution matrices are reflecting the fact that the likelihood of one amino acid being substituted with another during evolution varies and depends on the physical/chemical nature of the amino acid to be substituted. For example, the likelihood of a polar amino acid being substituted with another polar amino acid is higher compared to being substituted with a hydrophobic amino acid. Therefore, the scoring matrix will assign the highest score for identical amino acids, lower score for non-identical but similar amino acids and even lower score for non-identical non-similar amino acids. The most frequently used scoring matrices are the PAM matrices (Dayhoff et al. (1978), Jones et al. (1992)), the BLOSUM matrices (Henikoff and Henikoff (1992)) and the Gonnet matrix (Gonnet et al. (1992)).

Suitable computer programs for carrying out such an alignment include, but are not limited to, Vector NTI (Invitrogen Corp.) and the ClustalV, ClustalW and ClustalW2 programs (Higgins D G & Sharp P M (1988), Higgins et al. (1992), Thompson et al. (1994), Larkin et al. (2007). A selection of different alignment tools is available from the ExPASy Proteomics server at www.expasy.org. Another example of software that can perform sequence alignment is BLAST (Basic Local Alignment Search Tool), which is available from the webpage of National Center for Biotechnology Information which can currently be found at http://www.ncbi.nlm.nih.gov/and which was firstly described in Altschul et al. (1990) J. Mol. Biol. 215; 403-410.

Once the software has produced an alignment, it is possible to calculate % similarity and % sequence identity. The software typically does this as part of the sequence comparison and generates a numerical result.

In one embodiment, it is preferred to use the ClustalW software for performing sequence alignments. Preferably, alignment with ClustalW is performed with the following parameters for pairwise alignment:

| | |
|---|---|
| Substitution matrix: | Gonnet 250 |
| Gap open penalty: | 20 |
| Gap extension penalty: | 0.2 |
| Gap end penalty: | None |

ClustalW2 is for example made available on the internet by the European Bioinformatics Institute at the EMBL-EBI webpage www.ebi.ac.uk under tools—sequence analysis—ClustalW2. Currently, the exact address of the ClustalW2 tool is www.ebi.ac.uk/Tools/clustalw2.

In another embodiment, it is preferred to use the program Align X in Vector NTI (Invitrogen) for performing sequence alignments. In one embodiment, Exp10 has been may be used with default settings:
Gap opening penalty: 10
Gap extension penalty: 0.05
Gapseparation penalty range: 8
Score matrix: blosum62mt2

Thus, the present invention also encompasses the use of variants, fragments, and derivatives of any amino acid sequence of a protein, polypeptide, motif or domain as defined herein, particularly those of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34.

The sequences, particularly those of variants, fragments, and derivatives of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34, may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

The present invention also encompasses conservative substitution (substitution and replacement are both used herein to mean the interchange of an existing amino acid residue, with an alternative residue) that may occur i.e. like-for-like substitution such as basic for basic, acidic for acidic, polar for polar etc. Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as 0), pyriylalanine, thienylalanine, naphthylalanine and phenylglycine.

Conservative substitutions that may be made are, for example within the groups of basic amino acids (Arginine, Lysine and Histidine), acidic amino acids (glutamic acid and aspartic acid), aliphatic amino acids (Alanine, Valine, Leucine, Isoleucine), polar amino acids (Glutamine, Asparagine, Serine, Threonine), aromatic amino acids (Phenylalanine, Tryptophan and Tyrosine), hydroxyl amino acids (Serine, Threonine), large amino acids (Phenylalanine and Tryptophan) and small amino acids (Glycine, Alanine).

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-α-amino butyric acid*, L-γ-amino butyric acid*, L-α-amino isobutyric acid*, L-ϵ-amino caproic acid*, 7-amino heptanoic acid*, L-methionine sulfone*, L-norleucine*, L-norvaline*, p-nitro-L-phenylalanine*, L-hydroxyproline*, L-thioproline*, methyl derivatives of phenylalanine (Phe) such as 4-methyl-Phe*, pentamethyl-Phe*, L-Phe (4-amino)*, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-conservative substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al. (1992), Horwell D C. (1995).

In one embodiment, the variant targeting unit used in the homodimeric protein according to the present invention is variant having the sequence of amino acids at least 80%, at least 85%, at least 90%, at least 95%, at least 96%, at least 97%, at least 98% or at least 99% amino acid sequence identity therewith.

In one aspect, preferably the protein or sequence used in the present invention is in a purified form. The term "purified" means that a given component is present at a high level. The component is desirably the predominant active component present in a composition.

A "variant" or "variants" refers to proteins, polypeptides, units, motifs, domains or nucleic acids. The term "variant" may be used interchangeably with the term "mutant." Variants include insertions, substitutions, transversions, truncations, and/or inversions at one or more locations in the amino acid or nucleotide sequence, respectively. The phrases "variant polypeptide", "polypeptide", "variant" and "variant enzyme" mean a polypeptide/protein that has an amino acid sequence that has been modified from the amino acid sequence of SEQ ID NO: 1. The variant polypeptides include a polypeptide having a certain percent, e.g., 80%, 85%, 90%, 91%, 92%, 93%, 94%, 95%, 96%, 97%, 98%, or 99%, of sequence identity with the amino acid sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34.

"Variant nucleic acids" can include sequences that are complementary to sequences that are capable of hybridizing to the nucleotide sequences presented herein. For example, a variant sequence is complementary to sequences capable of hybridizing under stringent conditions, e.g., 50° C. and 0.2×SSC (1×SSC=0.15 M NaCl, 0.015 M sodium citrate, pH 7.0), to the nucleotide sequences presented herein. More particularly, the term variant encompasses sequences that are complementary to sequences that are capable of hybridizing under highly stringent conditions, e.g., 65° C. and 0.1×SSC, to the nucleotide sequences presented herein. The melting point (Tm) of a variant nucleic acid may be about 1, 2, or 3° C. lower than the Tm of the wild-type nucleic acid. The variant nucleic acids include a polynucleotide having a certain percent, e.g., 80%, 85%, 90%, 95%, or 99%, of sequence identity with the nucleic acid encoding SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:32, or SEQ ID NO:34, encoding the monomeric protein which can form the homodimeric protein according to invention.

A specific category of mutations are the mutations in E6 and E7:

The E6 protein may be detoxified by rendering the p53 binding impossible. Five positions in the full length HPV16 E6 protein are sites for mutations for inactivation of E6 functionality, F47, L50, C63, C106 and I128. Any amino acid substitution in these positions may lead to inactivation of E6 and induces tumor suppression. Substitutions in any one of these positions with any one different amino acid may potentially be utilized. Sites for potential mutations are shown in SEQ ID NO:22.

In the E7 protein there are conserved regions associated with oncogenic properties (see Phelps et al 3. Virol. April 1992, vol. 66, no. 42418-242; Gulliver et al J Virol. 1997, August; 71(8)) including an N-terminal Rb (retinoblastoma binding protein) binding-site motif (LXCXE) and two conserved regions 3 (upstream and downstream) with a Zn-binding motif (CXXC). The preferred mutation sites in the LXCXE-motif are C24 and E26. Preferred sites in the two CXXC motifs are C58, C61, C91 and C94. However, any mutations in these regions can be envisaged to be substituted for the reduction of binding functions and thus abolish the oncogenic effects of E7. Sites for potential mutations are shown in SEQ ID NO:23.

Signal Peptide:

A signal peptide at the N-terminal end of the nascent polypeptide directs the molecule into the ER before transport to into the Golgi complex. The signal peptide is cleaved off by signal peptidase once it has served its purpose of targeting and importing the protein to the ER. These signal peptides are generally between 15 and 30 amino acids, but can have more than 50 residues (Martoglio, B. et al., *Trends in Cell Biology*, 1998, Knappskog, S. et al., *J Biotechnol*, 2007). The native signal peptide may be replaced by signal peptides from any mammalian, prokaryotic or marine origin. Commonly used signal peptides are e.g. humanIL-2 and human albumin due to their natural ability to secrete large amounts of protein. The choice of signal peptide can have a considerable impact on the amount of synthesized and secreted protein.

In some embodiments, the signal peptide used in the protein construct according to the present invention is derived from a chemokine protein, such as the signal sequence of LD78beta.

In some embodiments the signal peptide is not derived from pLNOH2 (B1-8 variable immunoglobulin leader) disclosed in the international application with International Application No: PCT/EP2011/060628.

In some embodiments the signal peptide is not derived from an immunoglobulin gene.

The term "homodimeric protein" as used herein refers to a protein comprising two individual identical strands of amino acids, or subunits held together as a single, dimeric protein by hydrogen bonding, ionic (charged) interactions, actual covalent disulfide bonding, or some combination of these interactions.

The term "dimerization motif", as used herein, refers to the sequence of amino acids between the antigenic unit and the targeting unit comprising the hinge region and the optional second domain that may contribute to the dimerization. This second domain may be an immunoglobulin domain, and optionally the hinge region and the second domain are connected through a linker. Accordingly the dimerization motif serves to connect the antigenic unit and the targeting unit, but also contain the hinge region that facilitates the dimerization of the two monomeric proteins into a homodimeric protein according to the invention.

The term "targeting unit" as used herein refers to a unit that delivers the protein with its antigen to mouse or human APC for MHC class II-restricted presentation to CD4+ T cells or for providing cross presentation to CD8+ T cells by MHC class I restriction. The targeting unit used in the constructs according to the present invention is derived from or identical to mature LD78-beta.

The term "antigenic unit" as used herein refers to any molecule, such as a peptide which is able to be specifically recognized by an antibody or other component of the immune system, such as a surface receptor on T-cells. Included within this definition are also immunogens that are able to induce an immune response. The terms "epitope" or "antigenic epitope" is used to refer to a distinct molecular surface, such as a molecular surface provided by a short peptide sequence within an antigenic unit. In some embodiments the antigenic unit comprises two ore more antigenic epitopes. The antigenic unit used in the constructs according to the present invention is derived from or identical to the early gene products E6 and E7 from HPV, such as from HPV16 or HPV18.

The term "hinge region" refers to a peptide sequence of the homodimeric protein that facilitates the dimerization, such as through the formation of an interchain covalent bond(s), e.g. disulfide bridge(s). The hinge region may be Ig derived, such as hinge exons h1+h4 of an Ig, such as IgG3.

Specific Embodiments of the Invention

As described above, the present invention relates to a homodimeric protein of two identical amino acid chains, each amino acid chain comprising (1) a signal peptide, (2) a targeting unit, (3) a dimerization motif, and (4) an antigenic unit, said targeting unit comprising an amino acid sequence having at least 80% sequence identity to the amino acid sequence 24-93 of SEQ ID NO:1, and an antigenic unit comprising an amino acid sequence of human papillomavirus (HPV), such as an antigenic unit comprising an amino acid sequence of HPV16 and/or HPV18, such as an antigenic unit derived from early proteins E6 and/or E7 of HPV16 and/or HPV18. In some embodiments according to the present invention, the targeting unit, dimerization motif and antigenic unit in the amino acid chain are in the N-terminal to C-terminal order of targeting unit, dimerization motif and antigenic unit.

In some embodiments, the antigenic unit used in the constructs according to the present invention is derived from HPV16, such as from early proteins E6 and/or E7.

In some embodiments, the antigenic unit used in the constructs according to the present invention is derived from E6 of HPV16.

In some embodiments, the antigenic unit used in the constructs according to the present invention is derived from E7 of HPV16.

In some embodiments, the antigenic unit used in the constructs according to the present invention is derived from HPV18, such as from early proteins E6 and/or E7.

In some embodiments, the antigenic unit used in the constructs according to the present invention is derived from E6 of HPV18.

In some embodiments, the antigenic unit used in the constructs according to the present invention is derived from E7 of HPV18.

In some embodiments according to the present invention, the signal peptide consists of an amino acid sequence having at least 80% sequence identity to the amino acid sequence 1-23 of SEQ ID NO:1.

In some embodiments according to the present invention, the signal peptide consists of an amino acid sequence having at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99%, such as 100% sequence identity to the amino acid sequence 1-23 of SEQ ID NO:1.

In some embodiments according to the present invention, the targeting unit consists of an amino acid sequence having at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 24-93 of SEQ ID NO:1.

In some embodiments according to the present invention, the dimerization motif comprises a hinge region and optionally another domain that facilitate dimerization, such as an immunoglobulin domain, optionally connected through a linker.

In some embodiments according to the present invention, the hinge region is Ig derived, such as derived from IgG3.

In some embodiments according to the present invention, the hinge region has the ability to form one, two, or several covalent bonds. In some embodiments according to the present invention, the covalent bond is a disulphide bridge.

In some embodiments according to the present invention, the immunoglobulin domain of the dimerization motif is a carboxyterminal C domain, or a sequence that is substantially identical to the C domain or a variant thereof.

In some embodiments according to the present invention, the carboxyterminal C domain is derived from IgG.

In some embodiments according to the present invention, the immunoglobulin domain of the dimerization motif has the ability to homodimerize.

In some embodiments according to the present invention, the immunoglobulin domain has the ability to homodimerize via noncovalent interactions. In some embodiments according to the present invention, the noncovalent interactions are hydrophobic interactions.

In some embodiments according to the present invention, the dimerization domain does not comprise the CH2 domain.

In some embodiments according to the present invention, the dimerization motif consists of hinge exons h1 and h4 connected through a linker to a $C_H3$ domain of human IgG3.

In some embodiments according to the present invention, the dimerization motif consist of an amino acid sequence having at least 80% sequence identity to the amino acid sequence 94-237 of SEQ ID NO:3.

In some embodiments according to the present invention, the linker is a $G_3S_2G_3SG$ linker.

In some embodiments according to the present invention, the antigenic unit and the dimerization motif is connected through a linker, such as a GLGGL linker or a GLSGL linker.

In some embodiments according to the present invention, the targeting unit consists of amino acids 24-93 of SEQ ID NO:1, or a variant thereof.

In some embodiments according to the present invention, the homodimeric protein have increased affinity for any one chemokine receptor selected from CCR1, CCR3 and CCR5 as compared to the affinity of the same homodimeric protein with the targeting unit consisting of amino acids 24-93 of SEQ ID NO:1, or a variant thereof.

In some embodiments according to the present invention, the antigenic unit comprises an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-293 of SEQ ID NO:3.

In some embodiments according to the present invention, the antigenic unit consists of an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-293 of SEQ ID NO:3.

In some embodiments according to the present invention, the antigenic unit comprises one or more amino acid substitutions at a position selected from the list consisting of F47, L50, C63, C106 and I128 of SEQ ID NO:22, or a deletion involving one or more amino acid selected from the list consisting of Y43-L50 of SEQ ID NO:22.

In some embodiments according to the present invention, the antigenic unit comprises not more than 1, 2, 3, 4, 5, 6, 7, 8, 9, 10, 12, 14, 16, 18 or 20 amino acid substitutions and/or deletions relative to SEQ ID NO:22.

In some embodiments according to the present invention, the antigenic unit comprises the amino acid sequence 243-293 of SEQ ID NO:3, SEQ ID NO:5, SEQ ID NO:7, or SEQ ID NO:9, or a variant or antigenic fragment thereof.

In some embodiments according to the present invention, the antigenic unit consists of the amino acid sequence 243-293 of SEQ ID NO:3, SEQ ID NO:5, SEQ ID NO:7, or SEQ ID NO:9, or a variant or antigenic fragment thereof.

In some embodiments according to the present invention, the antigenic unit comprises an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-340 of SEQ ID NO:11.

In some embodiments according to the present invention, the antigenic unit consists of an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-340 of SEQ ID NO:11.

In some embodiments according to the present invention, the antigenic unit comprises one or more amino acid substitutions at a position selected from the list consisting of C24, E26, C58, C61, C91, and C94 of SEQ ID NO:23, or a deletion involving one or more amino acid selected from the list consisting of L22-E26 and/or C58-C61 and/or C91-595 of SEQ ID NO:23.

In some embodiments according to the present invention, the antigenic unit comprises not more than 1, 2, 3, 4, 5, 6, 7, 8, 9, 10, 12, 14, 16, 18 or 20 amino acid substitutions and/or deletions relative to SEQ ID NO:23.

In some embodiments according to the present invention, the antigenic unit comprises the amino acid sequence 243-340 of SEQ ID NO:11, SEQ ID NO:13, SEQ ID NO:15, or SEQ ID NO:17, or a variant or antigenic fragment thereof.

In some embodiments according to the present invention, the antigenic unit consists of the amino acid sequence 243-340 of SEQ ID NO:11, SEQ ID NO:13, SEQ ID NO:15, or SEQ ID NO:17, or a variant or antigenic fragment thereof.

In some embodiments according to the present invention, the antigenic unit comprises an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-501 of SEQ ID NO:19, SEQ ID NO:21, SEQ ID NO:32, or SEQ ID NO:34.

In some embodiments according to the present invention, the antigenic unit consists of an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to the amino acid sequence 243-501 of SEQ ID NO:19, SEQ ID NO:21, SEQ ID NO:32, or SEQ ID NO:34.

In some embodiments according to the present invention, the antigenic unit comprising an amino acid sequence of human papillomavirus 16 (HPV16) derived from both early proteins E6 and E7.

In some embodiments according to the present invention, the antigenic unit comprising an amino acid sequence of human papillomavirus 18 (HPV18) derived from both early proteins E6 and E7.

In some embodiments according to the present invention, the antigenic unit comprises one or more amino acid substitutions at a position selected from the list consisting of F47, L50G, C63, C106, I128T of SEQ ID NO:22 and C24, E26, C58, C61, C91, C94 of SEQ ID NO:23.

In some embodiments according to the present invention, the antigenic unit comprises not more than 1, 2, 3, 4, 5, 6, 7, 8, 9, 10, 12, 14, 16, 18 or 20 amino acid substitutions and/or deletions relative to SEQ ID NO:22 and SEQ ID NO:23.

In some embodiments according to the present invention, the antigenic unit consists of the amino acid sequence 243-501 of SEQ ID NO:19, SEQ ID NO:21, SEQ ID NO:32, or SEQ ID NO:34, or a variant or antigenic fragment thereof.

In some embodiments according to the present invention, the amino acid chain consists of an amino acid sequence selected from the list consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:32, and SEQ ID NO:34, or a variant or antigenic fragment thereof.

In some embodiments according to the present invention, the antigenic unit comprises an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to any one amino acid sequence selected from SEQ ID NO:22, SEQ ID NO:23, SEQ ID NO:24, and SEQ ID NO:25.

In some embodiments according to the present invention, the antigenic unit consist of an amino acid sequence having at least 80%, such as at least 81%, such as at least 82%, such as at least 83%, such as at least 84%, such as at least 85%, such as at least 86%, such as at least 87%, such as at least 88%, such as at least 89%, such as at least 90%, such as at least 91%, such as at least 92%, such as at least 93%, such as at least 94%, such as at least 95%, such as at least 96%, such as at least 97%, such as at least 98%, such as at least 99% sequence identity to any one amino acid sequence selected from SEQ ID NO:22, SEQ ID NO:23, SEQ ID NO:24, and SEQ ID NO:25.

In some embodiments the homodimeric protein according to the present invention, is in its mature form without any signal peptide sequence.

In some embodiments the nucleic acid molecule according to the present invention is human codon optimized.

It is to be understood that a human codon optimized nucleic acid molecule according to the present invention comprises one or more nucleic acid substitution as compared to the wild type sequence, which substitution provides for a codon with higher frequency of usage in human coding regions. Frequency of codon usage in homo sapiens can be found at http://biowiki.edu-wiki.org/en/codon_table In some embodiments the nucleic acid molecule according to the present invention is comprising any one of nucleotide sequences selected from the list consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:31 and SEQ ID NO:33, or a variant thereof.

In some embodiments the nucleic acid molecule according to the present invention is comprised by a vector.

In some embodiments the nucleic acid molecule according to the present invention is formulated for administration to a patient to induce production of the homodimeric protein in said patient.

In some embodiments the vaccine according to the present invention further comprises a pharmaceutically acceptable carrier and/or adjuvant.

In some embodiments, the method of treating or preventing a HPV induced disease or condition, such as a cancer or an infectious disease caused by HPV in a patient according to the present invention comprises administering to the patient in need thereof of a nucleic acid molecule, such as a DNA, according to the present invention with a subsequent step of electroporation. In some embodiments the administration is performed intra dermal or intra muscular.

Example 1

Construction and Expression of the Vaccines

Gene sequences were designed according to the following structure: 1: native leader sequence for human LD78 b, 2: full length LD78b sequence. 3: Human hinge-region 1 from IgG3. 4: Human hinge region 4 from IgG3. 5: Glycine-Serine linker. 6: Human CH3 domain from IgG3. 7: Glycine-Leucine linker. 8: wildtype and mutant Human papilloma virus oncogenes E6, E7 and fusion proteins of both E6 and E7 divided by a Glycine-Serine linker. The constructs are designated according to their E6 and or E7 composition as follows:

VB1001: Vaccibody-E6 wild type;
VB1005: Vaccibody-E7 wild type;
The mutants are designated according to the amino acid position in the corresponding native E6 or E7 sequence.
VB1002: Vaccibody-E6 C63R;
VB1003: Vaccibody-E6 C106R;
VB1004: Vaccibody-E6 F47R, C63R, C106R;
VB1006: Vaccibody-E7 C24G, E26G;
VB1007: Vaccibody-E7 C24G, E26G, C58G, C61G;
VB1008: Vaccibody-E7 C24G, E26G, C91G, C94G;
VB1009: Vaccibody-E7 C24G, E26G/E6 F47R, C63R, C106R;
VB1016: Vaccibody-E7 C24G, E26G/E6 C63R, C106R;

VB1020: Vaccibody-E7 C24G, E26G/E6 F47R, C63R, C106R human codon optimized

VB1021: Vaccibody-E7 C24G, E26G/E6 F47R, L50G, C106R, I128T human codon optimized Control vaccines composed of only the antigens were included:

Control 1: E7 C24G, E26G/E6 F47R, C63R, C106R;
Control 2: E7 C24G, E26G/E6 C63R, C106R All gene sequences were ordered from Aldevron (Fargo N. Dak., USA) or Eurofins MWG GmbH and cloned into the expression vector pUMVC4a.

All constructs were transfected in to 293E cells and verified expression of intact vaccibody proteins were performed by dot blot and ELISA (data not shown). All amino acid sequences except for Controls 1 and 2 are shown as SEQ IDs.

Example 2

Immune Response Studies

VB 1009, VB1016, VB1020 and VB1021 were selected as vaccine candidates with their corresponding controls 1 and 2 respectively. As a negative control empty pUMVC4a vector was utilized.

25, 12.5 and 1.4 µg plasmid DNA of each candidate was injected intradermal in the lower back of C57Bl/6 mice followed by electroporation, Dermavax, Cellectis (Paris, France). 7 days later the mice were boosted with similar amounts of vaccines and control plasmids. At day 21 the mice were killed and spleens were harvested.

The T cell responses were calculated by ELISPOT. (FIGS. 3a, b and c)

Example 3

Therapeutic Effect

VB1016, VB1020 and VB1021 with the corresponding controls 1 and 2 were selected as the vaccine candidate for therapeutic vaccine studies.

$5 \times 10^4$ or $5 \times 10^5$ TC-1 cells (Johns Hopkins University, Baltimore, USA, Lin K Y et al., *Cancer Res*, 1996) were injected in the neck or thigh region of C57Bl/6 mice. After days 3 and 10 or day 3,7 and 10, the mice were vaccinated with 2 µg, 10 µg, 12.5 µg or 20 µg of plasmid DNA followed by electroporation, Dermavax, Cellectis France. Tumor size were measured two to three times a week up until day 49 after TC-1 cell injection (FIGS. 4, 5 and 6)

Example 4

A therapeutic DNA vaccine to be used may be prepared by GMP manufacturing of the plasmid vaccine according to regulatory authorities' guidelines, including GMP cell banking, GMP manufacturing of drug substance and drug product, ICH stability studies and Fill & Finish of the DNA vaccine. The DNA vaccine may be formulated by dissolving in a saline solution, such as 10 nM Tris, 1 mM EDTA at a concentration of 2-5 mg/ml. The vaccine may be administered either intra-dermal or intra-muscular with or without following electroporation.

Sequences:

C-C motif chemokine 3-like 1 precursor including signal peptide (aa 1-23 in bold) and mature peptide (LD78-beta), aa 24-93 (SEQ ID NO:1):

```
MQVSTAALAVLLCTMALCNQVLSAPLAADTPTACCFSYTSRQIPQNFIAD

YFETSSQCSKPSVIFLTKRGRQVCADPSEEWVQKYVSDLELSA
```

The specific DNA and corresponding amino acid sequences of vaccibody HPV constructs:

E6 or E7 single constructs:

For the purpose of illustration only, the different domains of the constructs are separated by an "|" with the domains in the following order: Signal peptide human MIP-1α|Hinge h1|Hinge h4|Gly-Ser Linker or Gly-Leu linkers|hCH3 IgG3|Gly-Ser Linker or Gly-Leu linkers|wildtype or mutant full length E6 or E7. Amino acids or nucleotides in bold illustrates sites of mutations.

```
DNA sequence of VB1001 (SEQ ID NO: 2):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|GGCCTCGGTGGCCTG|ATGTTTCAGGACCCACAGGAGCGACCCAGAAAGTTACCACAGTTATGCACAGAGCTG

CAAACAACTATACATGATATAATATTAGAATGTGTGTACTGCAAGCAACAGTTACTGCGACGTGAGGTATATGACTTTG

CTTTTCGGGATTTATGCATAGTATATAGAGATGGGAATCCATATGCTGTATGTGATAAATGTTTAAAGTTTTATTCTAA

AATTAGTGAGTATAGACATTATTGTTATAGTTTGTATGGAACAACATTAGAACAGCAATACAACAAACCGTTGTGTGAT

TTGTTAATTAGGTGTATTAACTGTCAAAAGCCACTGTGTCCTGAAGAAAAGCAAAGACATCTGGACAAAAGCAAAGAT
```

-continued

TCCATAATATAAGGGGTCGGTGGACCGGTCGATGTATGTCTTGTTGCAGATCATCAAGAACACGTAGAGAAACCCAGCT

GTAA

Protein sequence of VB1001 (Homodimeric construct according to the
invention with E6, SEQ ID NO: 3): Amino acid sequence 393 amino acids.
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MFQDPQ

ERPRKLPQLCTELQTTIHDIILECVYCKQQLLRREVYDFAFRDLCIVYRDG

NPYAVCDKCLKFYSKISEYRHYCYSLYGTTLEQQYNKPLCDLLIRCINCQK

PLCPEEKQRHLDKKQRFHNIRGRWTGRCMSCCRSSRTRRETQL*

DNA sequence of VB1002 (SEQ ID NO: 4):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|*GGCCTCGGTGGCCTG*|ATGTTTCAGGACCCACAGGAGCGACCCAGAAAGTTACCACAGTTATGCACAGAGCTG

CAAACAACTATACATGATATAATATTAGAATGTGTGTACTGCAAGCAACAGTTACTGCGACGTGAGGTATATGACTTTG

CTTTTCGGGATTTATGCATAGTATATAGAGATGGAATCCATATGCTGTACGAGATAAATGTTTAAAGTTTTATTCTAA

AATTAGTGAGTATAGACATTATTGTTATAGTTTGTATGGAACAACATTAGAACAGCAATACAACAAACCGTTGTGTGAT

TTGTTAATTAGGTGTATTAACTGTCAAAAGCCACTGTGTCCTGAAGAAAAGCAAAGACATCTGGACAAAAAGCAAAGAT

TCCATAATATAAGGGGTCGGTGGACCGGTCGATGTATGTCTTGTTGCAGATCATCAAGAACACGTAGAGAAACCCAGCT

GTAA

Protein sequence of VB1002 (Homodimeric construct according to the
invention, SEQ ID NO: 5): Amino acid sequence, 393 amino acids.
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MFQDPQ

ERPRKLPQLCTELQTTIHDIILECVYCKQQLLRREVYDFAFRDLCIVYRDG

NPYAVRDKCLKFYSKISEYRHYCYSLYGTTLEQQYNKPLCDLLIRCINCQK

PLCPEEKQRHLDKKQRFHNIRGRWTGRCMSCCRSSRTRRETQL*

DNA sequence of VB 1003 (SEQ ID NO: 6):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

-continued

```
GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|GGCCTCGGTGGCCTG|ATGTTTCAGGACCCACAGGAGCGACCCAGAAAGTTACCACAGTTATGCACAGAGCTG

CAAACAACTATACATGATATAATATTAGAATGTGTGTACTGCAAGCAACAGTTACTGCGACGTGAGGTATATGACTTTG

CTTTTCGGGATTTATGCATAGTATATAGAGATGGGAATCCATATGCTGTATGTGATAAATGTTTAAAGTTTTATTCTAA

AATTAGTGAGTATAGACATTATTGTTATAGTTTGTATGGAACAACATTAGAACAGCAATACAACAAACCGTTGTGTGAT

TTGTTAATTAGGTGTATTAACCGACAAAAGCCACTGTGTCCTGAAGAAAAGCAAAGACATCTGGACAAAAAGCAAAGAT

TCCATAATATAAGGGGTCGGTGGACCGGTCGATGTATGTCTTGTTGCAGATCATCAAGAACACGTAGAGAAACCCAGCT

GTAA

Protein sequence of VB1003 (Homodimeric construct according to the
invention, SEQ ID NO: 7): Amino acid sequence, 393 amino acids.
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MFQDPQ

ERPRKLPQLCTELQTTIHDIILECVYCKQQLLRREVYDFAFRDLCIVYRDG

NPYAVCDKCLKFYSKISEYRHYCYSLYGTTLEQQYNKPLCDLLIRCINRQK

PLCPEEKQRHLDKKQRFHNIRGRWTGRCMSCCRSSRTRRETQL*

DNA sequence of VB1004 (SEQ ID NO: 8):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|GGCCTCGGTGGCCTG|ATGTTTCAGGACCCACAGGAGCGACCCAGAAAGTTACCACAGTTATGCACAGAGCTG

CAAACAACTATACATGATATAATATTAGAATGTGTGTACTGCAAGCAACAGTTACTGCGACGTGAGGTATATGACTTTG

CTCGACGGGATTTATGCATAGTATATAGAGATGGGAATCCATATGCTGTACGAGATAAATGTTTAAAGTTTTATTCTAA

AATTAGTGAGTATAGACATTATTGTTATAGTTTGTATGGAACAACATTAGAACAGCAATACAACAAACCGTTGTGTGAT

TTGTTAATTAGGTGTATTAACCGACAAAAGCCACTGTGTCCTGAAGAAAAGCAAAGACATCTGGACAAAAAGCAAAGAT

TCCATAATATAAGGGGTCGGTGGACCGGTCGATGTATGTCTTGTTGCAGATCATCAAGAACACGTAGAGAAACCCAGCT

GTAA

Protein sequence of VB1004 (Homodimeric construct according to the
invention, SEQ ID NO: 9): Amino acid sequence, 393 amino acids.
MQVSTAALAVLLCTMALCNQVLSAPLAADTPTACCFSYTSRQIPQNFIAD
```

-continued

YFETSSQCSKPSVIFLTKRGRQVCADPSEEWVQKYVSDLELSAELKTPLG

DTTHTEPKSCDTPPPCPRCPGGGSSGGGSGGQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGKGLGGLMFQDPQER

PRKLPQLCTELQTTIHDIILECVYCKQQLLRREVYDFARRDLCIVYRDGN

PYAVRDKCLKFYSKISEYRHYCYSLYGTTLEQQYNKPLCDLLIRCINRQK

PLCPEEKQRHLDKKQRFHNIRGRWTGRCMSCCRSSRTRRETQL*

DNA sequence of VB1005 (SEQ ID NO: 10):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|*GGCCTCGGTGGCCTG*|ATGCATGGAGATACACCTACATTGCATGAATATATGTTAGATTTGCAACCAGAGACA

ACTGATCTCTACTGTTATGAGCAATTAAATGACAGCTCAGAGGAGGAGGATGAAATAGATGGTCCAGCTGGACAAGCAG

AACCGGACAGAGCCCATTACAATATTGTAACCTTTTGTTGCAAGTGTGACTCTACGCTTCGGTTGTGCGTACAAAGCAC

ACACGTAGACATTCGTACTTTGGAAGACCTGTTAATGGGCACACTAGGAATTGTGTGCCCCATCTGTTCTCAGAAACCA

TAA

Protein sequence of VB1005 (Homodimeric construct according to the
invention with E7, SEQ ID NO: 11): Amino acid sequence, 340 amino acids.
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MHGDTP

TLHEYMLDLQPETTDLYCYEQLNDSSEEEDEIDGPAGQAEPDRAHYNIVTF

CCKCDSTLRLCVQSTHVDIRTLEDLLMGTLGIVCPICSQKP*

DNA sequence of VB1006 (SEQ ID NO: 12):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|*GGCCTCGGTGGCCTG*|ATGCATGGAGATACACCTACATTGCATGAATATATGTTAGATTTGCAACCAGAGACA

ACTGATCTCTACGGATATGGACAATTAAATGACAGCTCAGAGGAGGAGGATGAAATAGATGGTCCAGCTGGACAAGCAG

AACCGGACAGAGCCCATTACAATATTGTAACCTTTTGTTGCAAGTGTGACTCTACGCTTCGGTTGTGCGTACAAAGCAC

ACACGTAGACATTCGTACTTTGGAAGACCTGTTAATGGGCACACTAGGAATTGTGTGCCCCATCTGTTCTCAGAAACCA

TAA

Protein sequence of VB1006 (Homodimeric construct according to the
invention, SEQ ID NO: 13): Amino acid sequence, 340 amino acids.
MQVSTAALAVLLCTMALCNQVLSAPLAADTPTACCFSYTSRQIPQNFIAD

YFETSSQCSKPSVIFLTKRGRQVCADPSEEWVQKYVSDLELSAELKTPLG

DTTHTEPKSCDTPPPCPRCPGGGSSGGGSGGQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGKGLGGLMHGDTPTL

HEYMLDLQPETTDLYGYGQLNDSSEEEDEIDGPAGQAEPDRAHYNIVTFC

CKCDSTLRLCVQSTHVDIRTLEDLLMGTLGIVCPICSQKP*

DNA sequence of VB1007 (SEQ ID NO: 14):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|*GGCCTCGGTGGCCTG*|ATGCATGGAGATACACCTACATTGCATGAATATATGTTAGATTTGCAACCAGAGACA

ACTGATCTCTACGGATATGGACAATTAAATGACAGCTCAGAGGAGGAGGATGAAATAGATGGTCCAGCTGGACAAGCAG

AACCGGACAGAGCCCATTACAATATTGTAACCTTTGGATGCAAGGGAGACTCTACGCTTCGGTTGTGCGTACAAAGCAC

ACACGTAGACATTCGTACTTTGGAAGACCTGTTAATGGGCACACTAGGAATTGTGTGCCCCATCTGTTCTCAGAAACCA

TAA

Protein sequence of VB1007 (Homodimeric construct according to the
invention, SEQ ID NO: 15): Amino acid sequence, 340 amino acids.
MQVSTAALAVLLCTMALCNQVLSAPLAADTPTACCFSYTSRQIPQNFIAD

YFETSSQCSKPSVIFLTKRGRQVCADPSEEWVQKYVSDLELSAELKTPLG

DTTHTEPKSCDTPPPCPRCPGGGSSGGGSGGQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGKGLGGLMHGDTPTL

HEYMLDLQPETTDLYGYGQLNDSSEEEDEIDGPAGQAEPDRAHYNIVTFG

CKGDSTLRLCVQSTHVDIRTLEDLLMGTLGIVCPICSQKP*

DNA sequence of VB1008 (SEQ ID NO: 16):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

-continued
```
GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|GGCCTCGGTGGCCTG|ATGCATGGAGATACACCTACATTGCATGAATATATGTTAGATTTGCAACCAGAGACA

ACTGATCTCTACGGATATGGACAATTAAATGACAGCTCAGAGGAGGAGGATGAAATAGATGGTCCAGCTGGACAAGCAG

AACCGGACAGAGCCCATTACAATATTGTAACCTTTTGTTGCAAGTGTGACTCTACGCTTCGGTTGTGCGTACAAAGCAC

ACACGTAGACATTCGTACTTTGGAAGACCTGTTAATGGGCACACTAGGAATTGTGGGACCCATCGGATCTCAGAAACCA

TAA

Protein sequence of VB1008 (Homodimeric construct according to the
invention, SEQ ID NO: 17): Amino acid sequence, 340 amino acids.
MQVSTAALAVLLCTMALCNQVLSAPLAADTPTACCFSYTSRQIPQNFIAD

YFETSSQCSKPSVIFLTKRGRQVCADPSEEWVQKYVSDLELSAELKTPLG

DTTHTEPKSCDTPPPCPRCPGGGSSGGGSGGQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGKGLGGLMHGDTPTL

HEYMLDLQPETTDLYGYG**QLNDSSEEEDEIDGPAGQAEPDRAHYNIVTFC

CKCDSTLRLCVQSTHVDIRTLEDLLMGTLGIVGPIGSQKP*
```

Constructs with E6 and E7:

For the purpose of illustration only, the different domains of the constructs are separated by an "|" with the domains in the following order: Signal peptide|human MIP-1α|Hinge h1|Hinge h4|Gly-Ser Linker or Gly-Leu linker|hCH3 IgG3|Gly-Ser Linker or Gly-Leu linker|E7 mutant|Gly-Ser Linker or Gly-Leu linker|E6 mutant. Amino acids or nucleotides in bold illustrates sites of mutations.

```
DNA sequence of VB1009 (SEQ ID NO: 18):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|GGCCTCGGTGGCCTG|ATGCATGGAGATACACCTACATTGCATGAATATATGTTAGATTTGCAACCAGAGACA

ACTGATCTCTACGGATATGGACAATTAAATGACAGCTCAGAGGAGGAGGATGAAATAGATGGTCCAGCTGGACAAGCAG

AACCGGACAGAGCCCATTACAATATTGTAACCTTTTGTTGCAAGTGTGACTCTACGCTTCGGTTGTGCGTACAAAGCAC

ACACGTAGACATTCGTACTTTGGAAGACCTGTTAATGGGCACACTAGGAATTGTGTGCCCCATCTGTTCTCAGAAACCA

|GGCGGTGGAAGCAGCGGAGGTGGAAGTGGA|ATGTTTCAGGACCCACAGGAGCGACCCAGAAAGTTACCACAGTTATG

CACAGAGCTGCAAACAACTATACATGATATAATATTAGAATGTGTGTACTGCAAGCAACAGTTACTGCGACGTGAGGTA

TATGACTTTGCTCGACGGGATTTATGCATAGTATATAGAGATGGGAATCCATATGCTGTACGAGATAAATGTTTAAAGT

TTTATTCTAAAATTAGTGAGTATAGACATTATTGTTATAGTTTGTATGGAACAACATTAGAACAGCAATACAACAAACC

GTTGTGTGATTTGTTAATTAGGTGTATTAACCGACAAAAGCCACTGTGTCCTGAAGAAAAGCAAAGACATCTGGACAAA

AAGCAAAGATTCCATAATATAAGGGGTCGGTGGACCGGTCGATGTATGTCTTGTTGCAGATCATCAAGAACACGTAGAG

AAACCCAGCTGTAA
```

Protein sequence of VB1009 (Homodimeric construct according to the
invention, SEQ ID NO: 19): Amino acid sequence, 501 amino acids.
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MHGDTP

TLHEYMLDLQPETTDLYGYGQLNDSSEEEDEIDGPAGQAEPDRAHYNIVTF

CCKCDSTLRLCVQSTHVDIRTLEDLLMGTLGIVCPICSQKP|GGGSSGGGS

G|MFQDPQERPRKLPQLCTELQTTIHDIILECVYCKQQLLRREVYDFARRD

LCIVYRDGNPYAVRDKCLKFYSKISEYRHYCYSLYGTTLEQQYNKPLCDLL

IRCINRQKPLCPEEKQRHLDKKQRFHNIRGRWTGRCMSCCRSSRTRRETQL*

DNA sequence of VB1016 (SEQ ID NO: 20):
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA|*GGCCTCGGTGGCCTG*|ATGCATGGAGATACACCTACATTGCATGAATATATGTTAGATTTGCAACCAGAGACA

ACTGATCTCTACGGATATGGACAATTAAATGACAGCTCAGAGGAGGAGGATGAAATAGATGGTCCAGCTGGACAAGCAG

AACCGGACAGAGCCCATTACAATATTGTAACCTTTTGTTGCAAGTGTGACTCTACGCTTCGGTTGTGCGTACAAAGCAC

ACACGTAGACATTCGTACTTTGGAAGACCTGTTAATGGGCACACTAGGAATTGTGTGCCCCATCTGTTCTCAGAAACCA

1GGCGGTGGAAGCAGCGGAGGTGGAAGTGGA|ATGTTTCAGGACCCACAGGAGCGACCCAGAAAGTTACCACAGTTATG

CACAGAGCTGCAAACAACTATACATGATATAATATTAGAATGTGTGTACTGCAAGCAACAGTTACTGCGACGTGAGGTA

TATGACTTTGCTTTTCGGGATTTATGCATAGTATATAGAGATGGGAATCCATATGCTGTACGAGATAAATGTTTAAAGT

TTTATTCTAAAATTAGTGAGTATAGACATTATTGTTATAGTTTGTATGGAACAACATTAGAACAGCAATACAACAAACC

GTTGTGTGATTTGTTAATTAGGTGTATTAACCGACAAAAGCCACTGTGTCCTGAAGAAAAGCAAAGACATCTGGACAAA

AAGCAAAGATTCCATAATATAAGGGGTCGGTGGACCGGTCGATGTATGTCTTGTTGCAGATCATCAAGAACACGTAGAG

AAACCCAGCTGTAA

Protein sequence of VB1016 (Homodimeric construct according to the
invention, SEQ ID NO: 21): Amino acid sequence, 501 amino acids
MQVSTAALAVLLCTMALCNQVLSAPLAADTPTACCFSYTSRQIPQNFIAD

YFETSSQCSKPSVIFLTKRGRQVCADPSEEWVQKYVSDLELSAELKTPLG

DTTHTEPKSCDTPPPCPRCPGGGSSGGGSGGQPREPQVYTLPPSREEMTK

NQVSLTCLVKGFYPSDIAVEWESSGQPENNYNTTPPMLDSDGSFFLYSKL

TVDKSRWQQGNIFSCSVMHEALHNRFTQKSLSLSPGKGLGGLMHGDTPTL

HEYMLDLQPETTDLYGYGQLNDSSEEEDEIDGPAGQAEPDRAHYNIVTFC

CKCDSTLRLCVQSTHVDIRTLEDLLMGTLGIVCPICSQKPGGGSSGGGSG

MFQDPQERPRKLPQLCTELQTTIHDIILECVYCKQQLLRREVYDFAFRDL

-continued

CIVYRDGNPYAVRDKCLKFYSKISEYRHYCYSLYGTTLEQQYNKPLCDLL

IRCINRQKPLCPEEKQRHLDKKQRFHNIRGRWTGRCMSCCRSSRTRRETQ

L*

SEQ ID NO: 22:
>tr|Q778I6|Q778I6_HPV16 E6 protein OS = Human papillomavirus type 16
GN = E6 PE = 4 SV = 1; (Underlined amino acids denotes amino acids
that may be deleted; Potential amino acids that may be mutated
are highlighted)
MFQDPQERPRKLPQLCTELQTTIHDIILECVYCKQQLLRREV<u>YDFAFRDL</u>CIVYRDGNPYAVCDKCLKFY

SKISEYRHYCYSLYGTTLEQQYNKPLCDLLIRCINCQKPLCPEEKQRHLDKKQRFHNIRGRWTGRCMSCC

RSSRTRRETQL

SEQ ID NO: 23:
>sp|P03129|VE7_HPV16 Protein E7 OS = Human papillomavirus type 16
GN = E7 PE = 1 SV = 1; (Underlined amino acids denotes amino acids
that may be deleted; Potential amino acids that may be mutated
are highlighted)
MHGDTPTLHEYMLDLQPETTD<u>LYCYE</u>QLNDSSEEEDEIDGPAGQAEPDRAHYNIVTFCCKCDSTLRLCVQ

STHVDIRTLEDLLMGTLGIVCPICSQKP

SEQ ID NO: 24:
>sp|P06463|VE6_HPV18 Protein E6 OS = Human papillomavirus
type 18 GN = E6 PE = 1 SV = 1
MARFEDPTRRPYKLPDLCTELNTSLQDIEITCVYCKTVLELTEVFEFAFKDLFVVYRDSI

PHAACHKCIDFYSRIRELRHYSDSVYGDTLEKLTNTGLYNLLIRCLRCQKPLNPAEKLRH

LNEKRRFHNIAGHYRGQCHSCCNRARQERLQRRRETQV

SEQ ID NO: 25:
>sp|P06788|VE7_HPV18 Protein E7 OS = Human papillomavirus
type 18 GN = E7 PE = 3 SV = 2
MHGPKATLQDIVLHLEPQNEIPVDLLCHEQLSDSEEENDEIDGVNHQHLPARRAEPQRHT

MLCMCCKCEARIKLVVESSADDLRAFQQLFLNTLSFVCPWCASQQ

SEQ ID NO: 26:
Hinge regions (IgG3 UH hinge), 12 amino acids:
ELKTPLGDTTHT

SEQ ID NO: 27:
Hinge region (IgG3, MH hinge, 15 amino acids):
EPKSCDTPPPCPRCP

SEQ ID NO: 28:
Gly-Ser Linker:
GGGSSGGGSG

SEQ ID NO: 29: hCH3 IgG3:
GQPREPQVYTLPPSREEMTKNQVSLTCLVKGFYPSDIAVEWESSGQPENNYNTTPPMLDSDGSFFLYSKL

TVDKSRWQQGNIFSCSVMHEALHNRFTQKSLSLSPGK

SEQ ID NO: 30: Linker:
GLGGL

SEQ ID NO: 31: DNA sequence of VB1020:
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

ATGAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

-continued

GTAAA|GGCCTCGGTGGCCTG/ATGCATGGCGATACCCCAACACTCCATGAGTACATGCTGGACCTTCAGCCCGAGAC

TACGGATCTGTATGGCTATGGGCAGTTGAATGACTCATCTGAGGAGGAGGACGAAATAGACGGCCCAGCTGGTCAAGCC

GAACCGGATAGAGCCCACTACAACATTGTGACCTTTTGCTGTAAGTGTGACAGCACTCTGAGACTGTGTGTTCAGTCCA

CTCATGTCGACATACGCACATTGGAGGATCTCCTGATGGGAACACTGGGAATTGTGTGTCCCATCTGTTCCCAAAAGCC

T/GGAGGTGGAAGCAGTGGAGGCGGTTCAGGC/ATGTTCCAAGATCCTCAAGAACGTCCTCGTAAGCTGCCACAGCTGT

GTACCGAGCTTCAGACCACCATTCACGACATCATCCTGGAGTGCGTCTATTGCAAACAGCAGCTCCTTAGAAGGGAAGT

GTACGATTTTGCACGGAGGGACCTCTGCATCGTGTATCGGGACGGCAATCCCTATGCGGTACGGGATAAATGCCTGAAG

TTCTACAGCAAAATCTCCGAGTACCGGCACTACTGCTACTCTCTCTATGGGACGACTCTGGAACAGCAGTACAACAAGC

CCTTGTGCGATCTGCTGATTCGCTGCATTAATCGCCAGAAACCTCTGTGCCCAGAAGAGAAGCAAAGACACCTGGACAA

GAAACAGCGATTCCACAACATCCGAGGGAGATGGACAGGGAGGTGTATGAGCTGCTGTCGGAGTTCTAGGACAAGGCGC

GAAACCCAGCTTTGA

SEQ ID NO: 32: Protein sequence of VB1020 (Homodimeric construct
according to the invention Amino acid sequence, 501 amino acids:
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MHGDTP

TLHEYMLDLQPETTDLYGYGQLNDSSEEEDEIDGPAGQAEPDRAHYNIVTF

CCKCDSTLRLCVQSTHVDIRTLEDLLMGTLGIVCPICSQKP|GGGSSGGGS

G|MFQDPQERPRKLPQLCTELQTTIHDIILECVYCKQQLLRREVYDFARRD

LCIVYRDGNPYAVRDKCLKFYSKISEYRHYCYSLYGTTLEQQYNKPLCDLL

IRCINRQKPLCPEEKQRHLDKKQRFHNIRGRWTGRCMSCCRSSRTRRETQL*

SEQ ID NO: 33: DNA sequence of VB1021:
ATGCAGGTCTCCACTGCTGCCCTTGCCGTCCTCCTCTGCACCATGGCTCTCTGCAACCAGGTCCTCTCT|GCACCACTT

GCTGCTGACACGCCGACCGCCTGCTGCTTCAGCTACACCTCCCGACAGATTCCACAGAATTTCATAGCTGACTACTTTG

AGACGAGCAGCCAGTGCTCCAAGCCCAGTGTCATCTTCCTAACCAAGAGAGGCCGGCAGGTCTGTGCTGACCCCAGTGA

GGAGTGGGTCCAGAAATACGTCAGTGACCTGGAGCTGAGTGCC|GAGCTCAAAACCCCACTTGGTGACACAACTCACAC

A|GAGCCCAAATCTTGTGACACACCTCCCCCGTGCCCAAGGTGCCCA|GGCGGTGGAAGCAGCGGAGGTGGAAGTGGA|

GGACAGCCCCGAGAACCACAGGTGTACACCCTGCCCCCATCCCGGGAGGAGATGACCAAGAACCAGGTCAGCCTGACCT

GCCTGGTCAAAGGCTTCTACCCCAGCGACATCGCCGTGGAGTGGGAGAGCAGCGGGCAGCCGGAGAACAACTACAACAC

CACGCCTCCCATGCTGGACTCCGACGGCTCCTTCTTCCTCTACAGCAAGCTCACCGTGGACAAGAGCAGGTGGCAGCAG

GGGAACATCTTCTCATGCTCCGTGATGCATGAGGCTCTGCACAACCGCTTCACGCAGAAGAGCCTCTCCCTGTCTCCGG

GTAAA/GGCCTCGGTGGCCTG/ATGCATGGTGACACACCAACCCTGCACGAATACATGCTCGATCTGCAGCCAGAGACT

ACCGACCTTTACGGCTATGGGCAGTTGAACGACAGCTCTGAGGAGGAGGACGAGATCGATGGTCCTGCTGGACAAGCAG

AACCAGACAGAGCCCACTACAACATCGTAACCTTTTGCTGCAAGTGTGACAGTACCCTTCGTTTGTGCGTTCAGAGCAC

GCATGTCGACATTCGGACACTGGAGGATCTGCTCATGGGACTCTGGGGATTGTGTGTCCTATTTGCAGCCAGAAACCA

/GGCGGAGGATCTTCAGGAGGCGGGAGTGGC/ATGTTCCAAGACCCTCAGGAACGCCCTCGGAAACTGCCCCAATTGTG

TACTGAGCTCCAGACAACGATACACGACATAATCCTGGAGTGCGTGTATTGCAAGCAGCAGCTTCTGAGGAGGGAAGTG

TACGATTTTGCCAGGAGAGATGGCTGCATTGTCTACCGAGATGGCAATCCCTATGCGGTGTGTGATAAGTGTCTGAAGT

TCTATTCCAAAATCAGCGAATATCGGCATTATTGCTACTCACTGTACGGAACTACCCTCGAACAGCAGTACAACAAACC

GCTCTGTGATCTGCTGATCAGATGCATCAATCGGCAGAAACCCCTTTGTCCCGAAGAGAAGCAAAGACACCTGGACAAG

AAGCAGAGGTTCCACAATACCCGAGGTCGTTGGACTGGGCGCTGCATGTCCTGTTGTCGCTCCTCTCGCACAAGGAGAG

AGACACAACTGTGA

SEQ ID NO: 34: Protein sequence of VB1021 (Homodimeric construct
according to the invention. Amino acid sequence, 501 amino acids:
MQVSTAALAVLLCTMALCNQVLS|APLAADTPTACCFSYTSRQIPQNFIAD

YFETSSQCSKPSVIFLTKRGRQVCADPSEEWVQKYVSDLELSA|ELKTPLG

DTTHT|EPKSCDTPPPCPRCP|GGGSSGGGSG|GQPREPQVYTLPPSREEM

TKNQVSLTCLVKGFYPSDIAVEWESSGQPENNYNTTPPMLDSDGSFFLYSK

LTVDKSRWQQGNIFSCSVMHEALHNRFTQKSLSLSPGK|GLGGL|MHGDTP

TLHEYMLDLQPETTDLYGYGQLNDSSEEEDEIDGPAGQAEPDRAHYNIVTF

CCKCDSTLRLCVQSTHVDIRTLEDLLMGTLGIVCPICSQKP|GGGSSGGGS

G|MFQDPQERPRKLPQLCTELQTTIHDIILECVYCKQQLLRREVYDFARRD

GCIVYRDGNPYAVCDKCLKFYSKISEYRHYCYSLYGTTLEQQYNKPLCDLL

IRCINRQKPLCPEEKQRHLDKKQRFHNTRGRWTGRCMSCCRSSRTRRETQL*

---

The invention claimed is:

1. A nucleic acid molecule, encoding an amino acid chain comprising (1) a signal peptide, (2) a targeting unit, (3) a dimerization motif, and (4) an antigenic unit, said targeting unit comprising an amino acid sequence having at least 80% sequence identity to the amino acid sequence 24-93 of SEQ ID NO:1, and an antigenic unit comprising an amino acid sequence having at least 80% sequence identity to early protein E6 (SEQ ID NO: 22) of HPV16 and an amino acid sequence having at least 80% sequence identity to early protein E7 (SEQ ID NO: 23) from HPV16, wherein the antigenic unit comprising an amino acid sequence having at least 80% sequence identity to early protein E6 further comprises the amino acid substitutions: F47R, C63R, and C106R.

2. The nucleic acid molecule according to claim 1, which nucleic acid molecule is human codon optimized.

3. A nucleic acid molecule comprising nucleotide sequence SEQ ID NO:31.

4. The nucleic acid molecule according to claim 1 formulated for administration to a patient to induce production of the homodimeric protein in said patients.

5. The nucleic acid molecule according to claim 1 being a DNA molecule.

6. The nucleic acid molecule according to claim 1 being a RNA molecule.

7. The nucleic acid molecule according to claim 1, wherein said targeting unit, dimerization motif and antigenic unit in said amino acid chain are in the N-terminal to C-terminal order of targeting unit, dimerization motif and antigenic unit.

8. The nucleic acid molecule according to claim 1, wherein said signal peptide consists of an amino acid sequence having at least 80% sequence identity to the amino acid sequence 1-23 of SEQ ID NO:1.

9. The nucleic acid molecule according to claim 1, wherein the dimerization motif comprises a hinge region and optionally another domain that facilitate dimerization, optionally connected through a linker.

10. The nucleic acid molecule according to claim 9, wherein the hinge region is an immunoglobulin domain.

11. The nucleic acid molecule according to claim 10, wherein the hinge region is derived from IgG3.

12. The nucleic acid molecule according to claim 1, wherein the dimerization motif consist of an amino acid sequence having at least 80% sequence identity to the amino acid sequence 94-237 of SEQ ID NO:3.

13. The nucleic acid molecule according to claim 1, wherein said antigenic unit and the dimerization motif is connected through a linker being a GLGGL linker or a GLSGL linker.

14. The nucleic acid molecule according to claim 1, wherein said antigenic unit comprises an amino acid sequence having at least 80% sequence identity to the amino acid sequence 243-293 of SEQ ID NO:3.

15. The nucleic acid molecule according to claim 1, wherein said antigenic unit comprises the amino acid sequence 243-293 of SEQ ID NO:3, SEQ ID NO:5, SEQ ID NO:7, or SEQ ID NO:9, or an antigenic fragment thereof.

16. The nucleic acid molecule according to claim 1, wherein said antigenic unit comprises an amino acid sequence having at least 80% sequence identity to the amino acid sequence 243-340 of SEQ ID NO:11.

17. The nucleic acid molecule according to claim 1, wherein said antigenic unit comprises the amino acid sequence 243-340 of SEQ ID NO:11, SEQ ID NO:13, SEQ ID NO:15, or SEQ ID NO:17, or an antigenic fragment thereof.

18. The nucleic acid molecule according to claim 1, wherein said antigenic unit further comprises one or more amino acid substitutions at a position selected from the list consisting of L50 and I128 of SEQ ID NO:22, or a deletion involving one or more amino acid selected from the list consisting of Y43-L50 of SEQ ID NO:22.

19. The nucleic acid molecule according to claim 1, wherein said antigenic unit further comprises one or more amino acid substitutions at a position selected from the list consisting of C24, E26, C58, C61, C91, and C94 of SEQ ID NO:23, or a deletion involving one or more amino acid selected from the list consisting of L22-E26 and/or C58-C61 and/or C91-S95 of SEQ ID NO:23.

20. The nucleic acid molecule according to claim 1, wherein said antigenic unit further comprises one or more amino acid substitutions at a position selected from the list consisting of L50 and I128 of SEQ ID NO:22 and C24, E26, C58, C61, C91, C94 of SEQ ID NO:23.

21. The nucleic acid molecule according to claim 1, wherein said antigenic unit comprises an amino acid sequence having at least 80% sequence identity to the amino acid sequence 243-501 of SEQ ID NO:19, SEQ ID NO:32, or SEQ ID NO:34.

22. The nucleic acid molecule according to claim 1, wherein said amino acid chain consists of amino acid sequence SEQ ID NO:32.

* * * * *